US012588959B2

(12) United States Patent
Sprenger et al.

(10) Patent No.: US 12,588,959 B2
(45) Date of Patent: Mar. 31, 2026

(54) SURGICAL INSTRUMENT WITH MAGNETIC SENSING

(71) Applicant: Auris Health, Inc., Redwood City, CA (US)

(72) Inventors: Jake Sprenger, Etobicoke (CA); Adam Hoffman, San Jose, CA (US); Andrew S. Berkowitz, Redwood City, CA (US); Lewis Theodore Cronis, Mendon, MA (US)

(73) Assignee: Auris Health, Inc., Santa Clara, CA (US)

( * ) Notice: Subject to any disclaimer, the term of this patent is extended or adjusted under 35 U.S.C. 154(b) by 290 days.

(21) Appl. No.: 18/320,025

(22) Filed: May 18, 2023

(65) Prior Publication Data

US 2024/0382272 A1     Nov. 21, 2024

(51) Int. Cl.
| | |
|---|---|
| *A61B 34/30* | (2016.01) |
| *A61B 17/00* | (2006.01) |
| *A61B 17/28* | (2006.01) |
| *A61B 17/29* | (2006.01) |

(52) U.S. Cl.
CPC .............. *A61B 34/30* (2016.02); *A61B 17/28* (2013.01); *A61B 2017/00477* (2013.01); *A61B 2017/2901* (2013.01)

(58) Field of Classification Search
CPC .................... A61B 34/30; A61B 17/28; A61B 2017/00477; A61B 2017/2901
See application file for complete search history.

(56) References Cited

U.S. PATENT DOCUMENTS

| | | |
|---|---|---|
| 9,763,741 B2 | 9/2017 | Alvarez et al. |
| 2015/0201918 A1 | 7/2015 | Kumar et al. |
| 2019/0000478 A1* | 1/2019 | Messerly ............... A61B 18/00 |
| 2020/0275997 A1 | 9/2020 | Cosse |
| 2021/0393361 A1 | 12/2021 | Keim et al. |
| 2022/0378522 A1 | 12/2022 | Zemlok et al. |

FOREIGN PATENT DOCUMENTS

WO        2022/144296 A1     7/2022

OTHER PUBLICATIONS

International Search Report and Written Opinion dated Aug. 30, 2024, for International Application No. PCT/IB2024/054800, 7 pages.

* cited by examiner

*Primary Examiner* — Carl H Layno
*Assistant Examiner* — Bryan Mcallister Lee
(74) *Attorney, Agent, or Firm* — FBT Gibbons LLP

(57) ABSTRACT

A sensor array can detect a position of a magnetic element. The sensor array can include a printed circuit board and a plurality of sensors. The printed circuit board is configured to rotate about a rotation axis and relative to the magnetic element. The plurality of sensors are disposed circumferentially about the rotation axis and coupled to the printed circuit board. At least one sensor is disposed at a selected circumferential position relative to the rotation axis. The sensor is configured to change between an open state and a closed state in response to a change in the position of the magnetic element relative to the rotation axis.

20 Claims, 27 Drawing Sheets

1

SURGICAL INSTRUMENT WITH MAGNETIC SENSING

TECHNICAL FIELD

Systems and methods disclosed herein related to surgical instruments, and more particularly to magnetic input sensing for surgical instruments.

BACKGROUND

Minimally invasive procedures allow for access to a targeted site within a patient with minimal trauma to the patient. A medical robotic system can provide a mechanism through which one or more robotic arms are used to perform a surgical operation. For example, laparoscopic surgery can allow for surgical access to a patient's cavity through a small incision on the patient's abdomen.

In some applications, certain conventional laparoscopes for use with robotic systems may include an interface, such as a tool drive adapter, to couple the laparoscope to the robotic system and allow the robotic system to control operation of the laparoscope. In some applications, the tool drive adapter can couple to the robotic system and allow the instrument shaft of the laparoscope to pass through and rotate relative to the tool driver assembly. In some applications, certain electronics may be sealed, isolated, or otherwise disposed within the instrument shaft to allow the laparoscope to be sterilized.

In some applications, certain conventional laparoscopes may contain a separate user interface to allow a clinician to control operations or functions of the laparoscope or the robotic system. The user interface may include one or more buttons or other elements a clinician can interact with. In some applications, certain conventional laparoscopes can contain electronic components to detect actuation of the buttons or other elements by the clinicians. In some applications, an end of the instrument shaft can be coupled to an end of the user interface, allowing the instrument shaft to rotate relative to the end of the user interface.

In some applications, since certain conventional robotic laparoscopes or surgical instruments include a tool driver adapter and a separate user interface attached to the end of the instrument shaft, certain conventional robotic surgical instruments may have an overall longer length than surgical instruments configured for manual use.

SUMMARY

Some predicate systems can utilize laparoscopes or other surgical instruments that that are unwieldy to handle and may not be sterilized utilizing standardized processes due to the additional length of the instrument attributed to a separate user interface attached to an end of the instrument shaft.

In accordance with some embodiments disclosed herein is the realization that as robotic systems and surgical instruments developed by the present Applicant continue to evolve and provide functionality hitherto unavailable, important and unexpected changes to the structure and architecture of the robotic system and surgical instruments were discovered and found to provide surprisingly important and advantageous results in facilitating the effective and simple operations of the robotic system and surgical instruments. Further, in accordance with some embodiments disclosed herein is the realization that a reduced overall instrument length, while maintaining a desired operational length is desired. Additionally, in accordance with some embodiments disclosed herein is the realization that combining a user interface with a tool drive adapter that can withstand sterilization while providing accurate detection of user inputs is desired. As such, the present disclosure addresses these and other challenges.

For example, due to the unique architecture of embodiments of the surgical instruments developed by the present Applicant, unique and innovative architecture has made it possible for overall length of the surgical instrument to be reduced, while maintaining a desired operational length. As a result, a robotic system can utilize the surgical instrument for a desired procedure, while allowing for the surgical instrument to be easily handled by a clinician and to be sterilized by utilizing standardized procedures and equipment. Further, the robotic system can utilize a surgical instrument that can provide accurate detection of user feedback, while allowing the components of the surgical instrument to withstand sterilization procedures.

Accordingly, embodiments disclosed herein provide a laparoscope or other surgical instrument can incorporate one or more user inputs (e.g. buttons) with the tool drive adapter, eliminating the need for a separate user interface, thereby reducing the overall length of the surgical instrument. The surgical instrument can include one or more sensors disposed, sealed, or isolated within an instrument shaft to detect the position or state of the user inputs, even as the instrument shaft rotates relative to the user inputs. The sensors can be arranged to provide reliable detection of the position or state of the user inputs.

Advantageously, some embodiments of the surgical instrument and sensor arrangement disclosed herein can reduce the overall length of the surgical instrument, while allowing for reliable detection of user inputs and withstanding sterilization processes. Such surgical instrument configurations and/or sensor arrangements can provide a solution to the above-noted challenges and have not been disclosed or implemented in predicate systems given that such systems did not implement or otherwise contemplate the unique improvements of Applicant's new technology until the discovery and development of embodiments of the instrument configurations and/or sensor arrangements described herein.

In accordance with some embodiments, a surgical instrument can include an instrument shaft and a tool drive adapter. The tool drive adapter can include a housing that is disposed around a portion of the instrument shaft. The instrument shaft can rotate about a rotation axis relative to the tool drive housing. In some embodiments, the surgical instrument is a laparoscope. Further, in some embodiments, the instrument shaft is a laparoscopic instrument.

In accordance with some embodiments, an actuator coupled to the tool drive housing can control a function of the surgical instrument. In some embodiments, a sensor array disposed within or otherwise coupled to the instrument shaft can detect a position of the actuator or any other suitable magnetic element. The sensor array can be disposed within or otherwise coupled to any suitable instrument, tool, or device.

The sensor array can include a printed circuit board configured to rotate about a rotation axis and relative to the magnetic element. In some embodiments, the printed circuit board can be round.

In accordance with some embodiments, a plurality of sensors can be disposed about the rotation axis and coupled to the printed circuit board. One or more sensors can be configured to change between an open state and a closed state in response to a change in position of the magnetic element relative to the rotation axis or provide a signal corresponding to the actuation of the actuator. The sensors can be equidistantly spaced apart. In some applications, the sensor array can include multiple groups of sensors. For example, in some embodiments, one group of sensors may be disposed on a first surface of a printed circuit board, and another group of sensors can be disposed on an opposite second surface of the printed circuit board. One group of sensors may be interposed between another group of sensors. In some applications, the sensors are reed switches.

In some embodiments, the printed circuit board can include a plurality of elongated slats disposed circumferentially about the rotation axis and configured to rotate about the rotation axis and relative to the magnetic element. In some embodiments, sensors can be coupled to a respective elongated slat of the plurality of elongated slats. In accordance with some embodiments, sensors can be disposed on the elongated slats. The sensors can be laterally spaced apart along the rotation axis.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved case of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
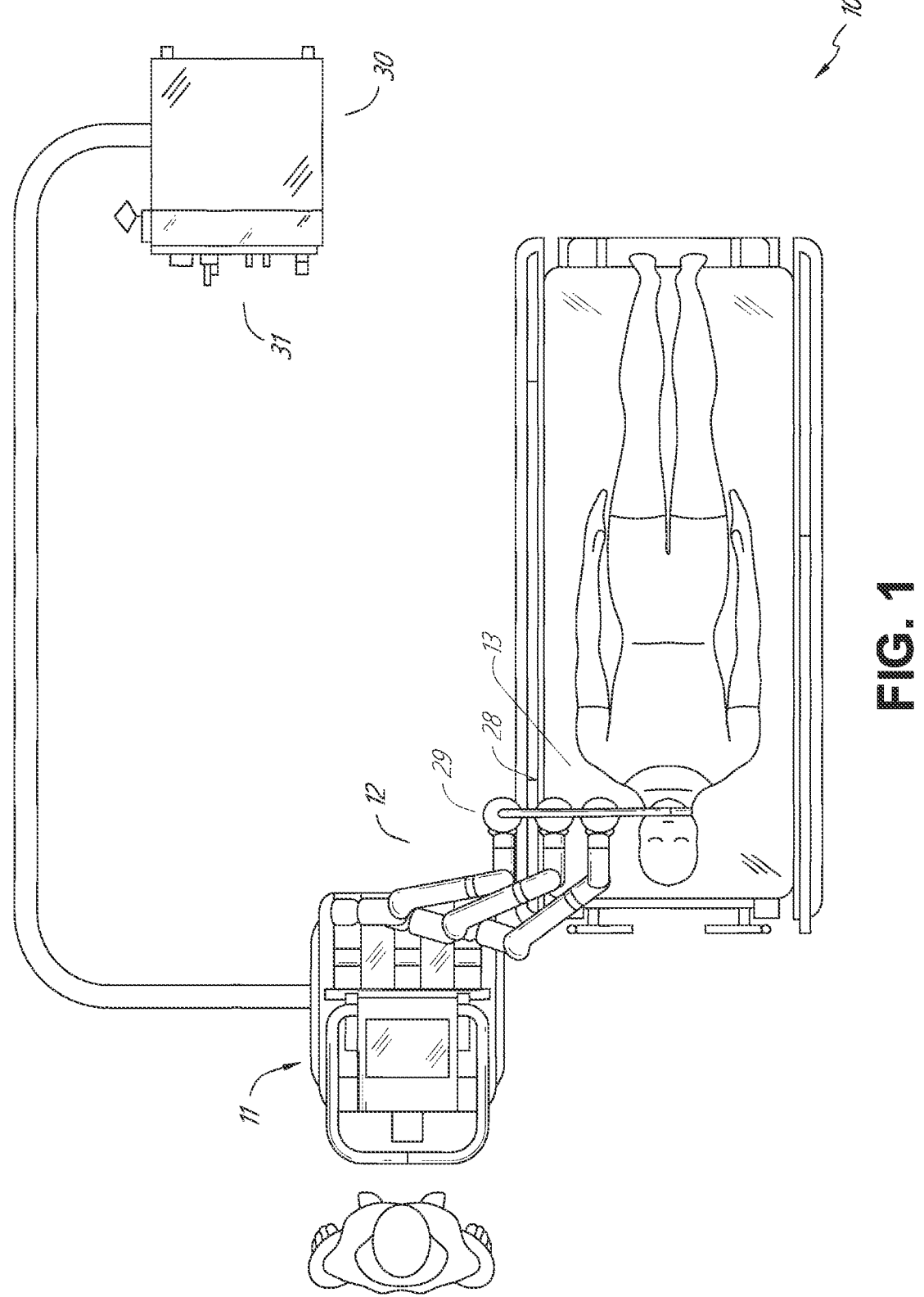
FIG. 1 illustrates an embodiment of a cart-based robotic system arranged for diagnostic and/or therapeutic bronchoscopy procedure(s).
Figure 2:
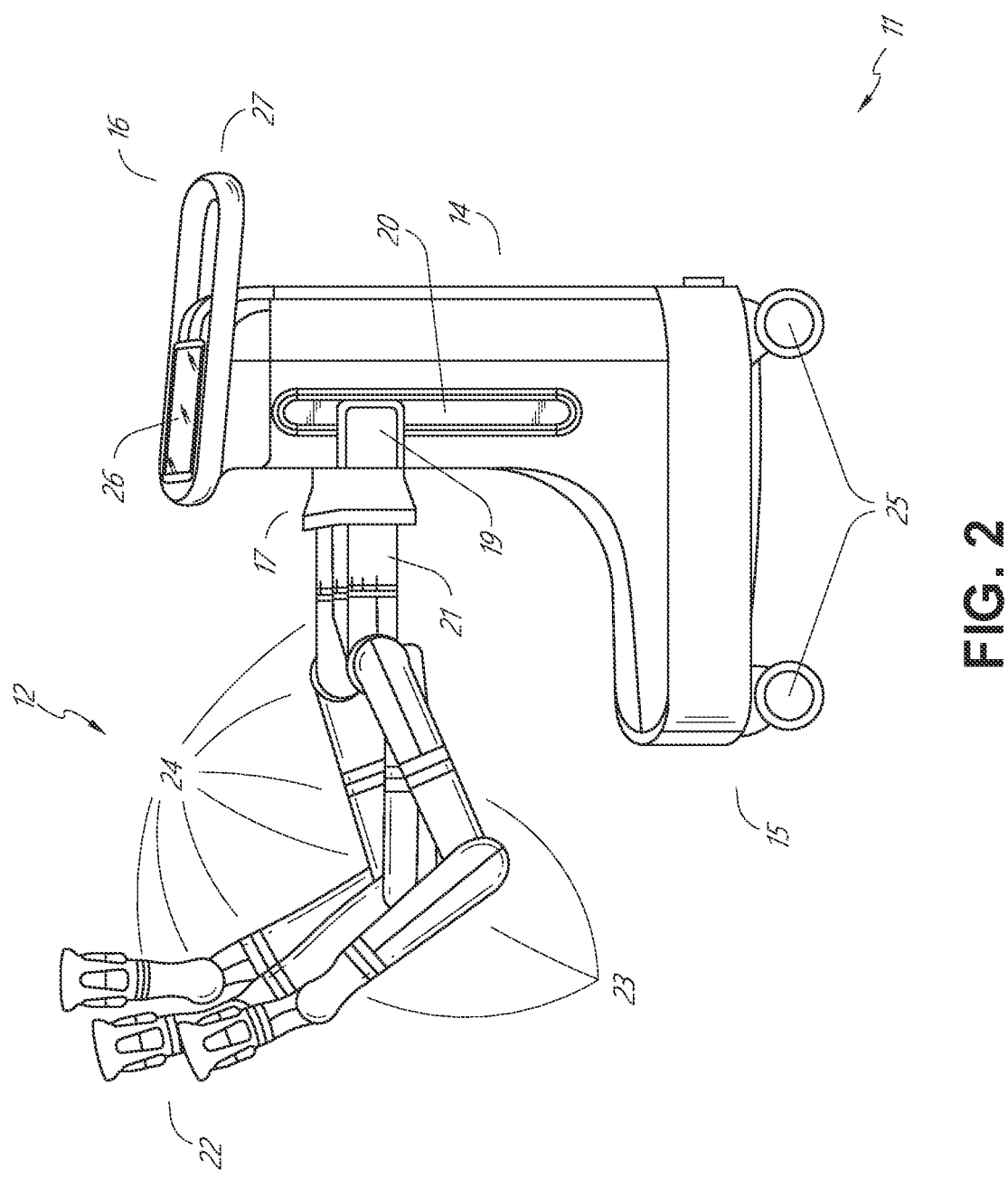
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
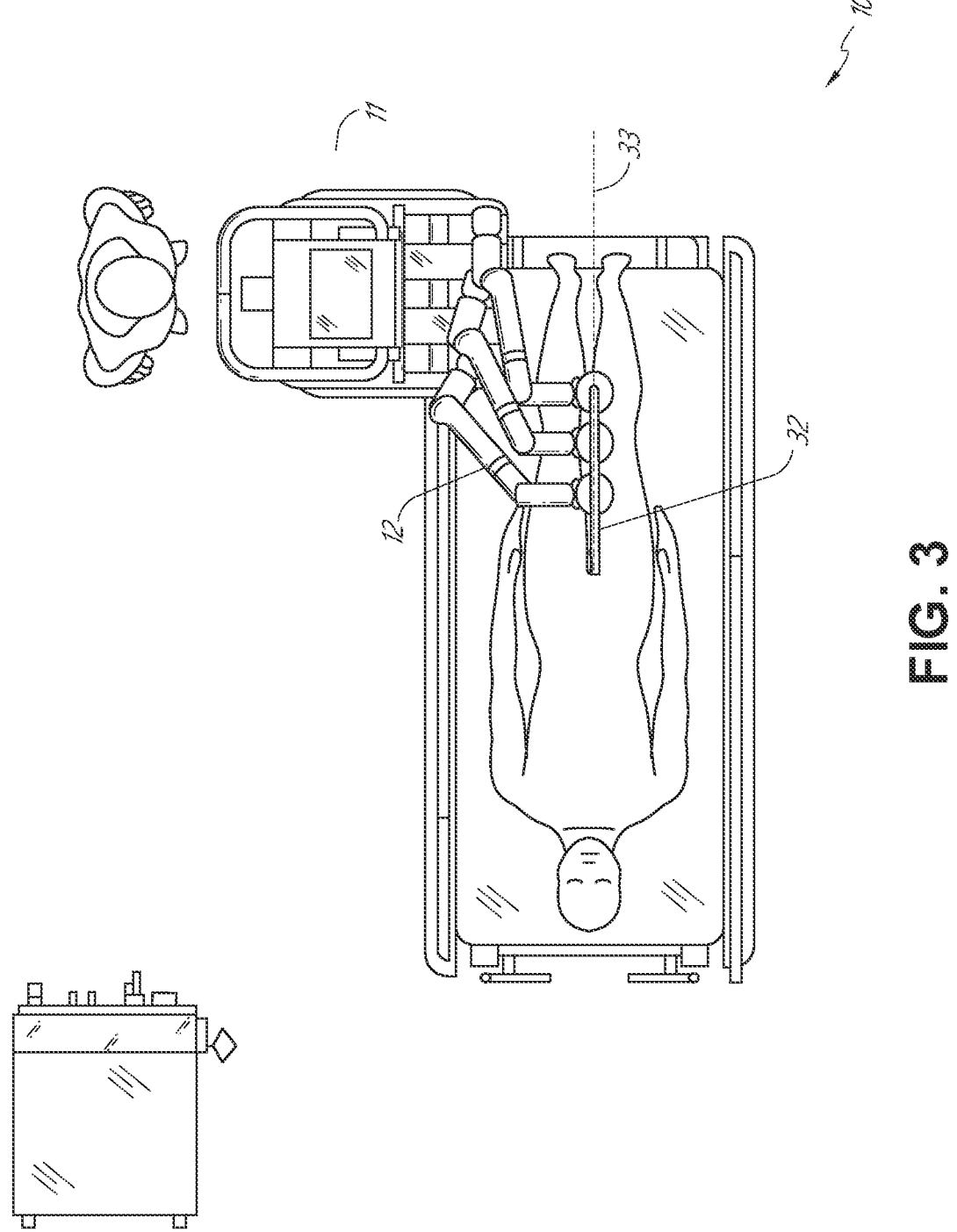
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
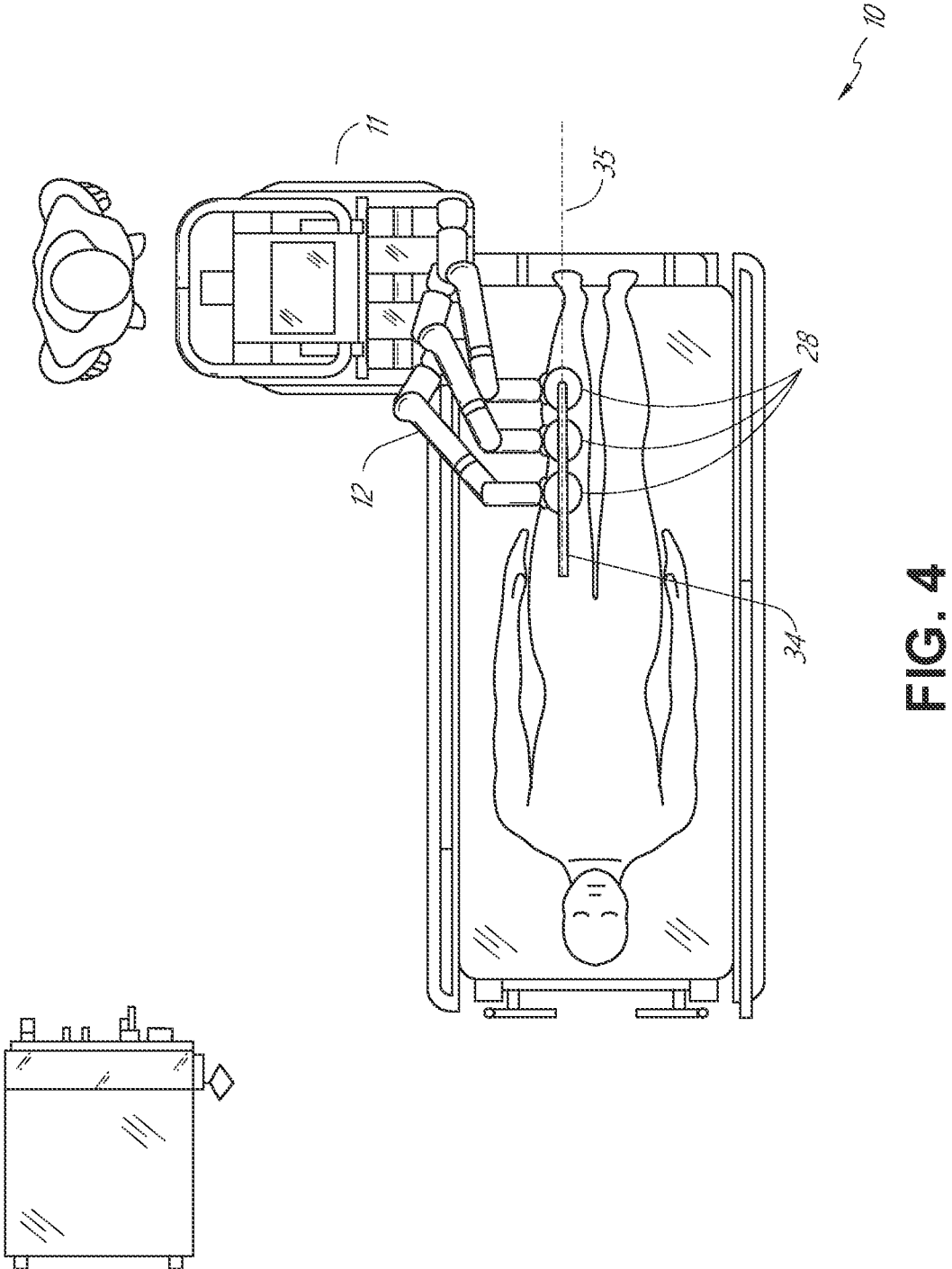
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
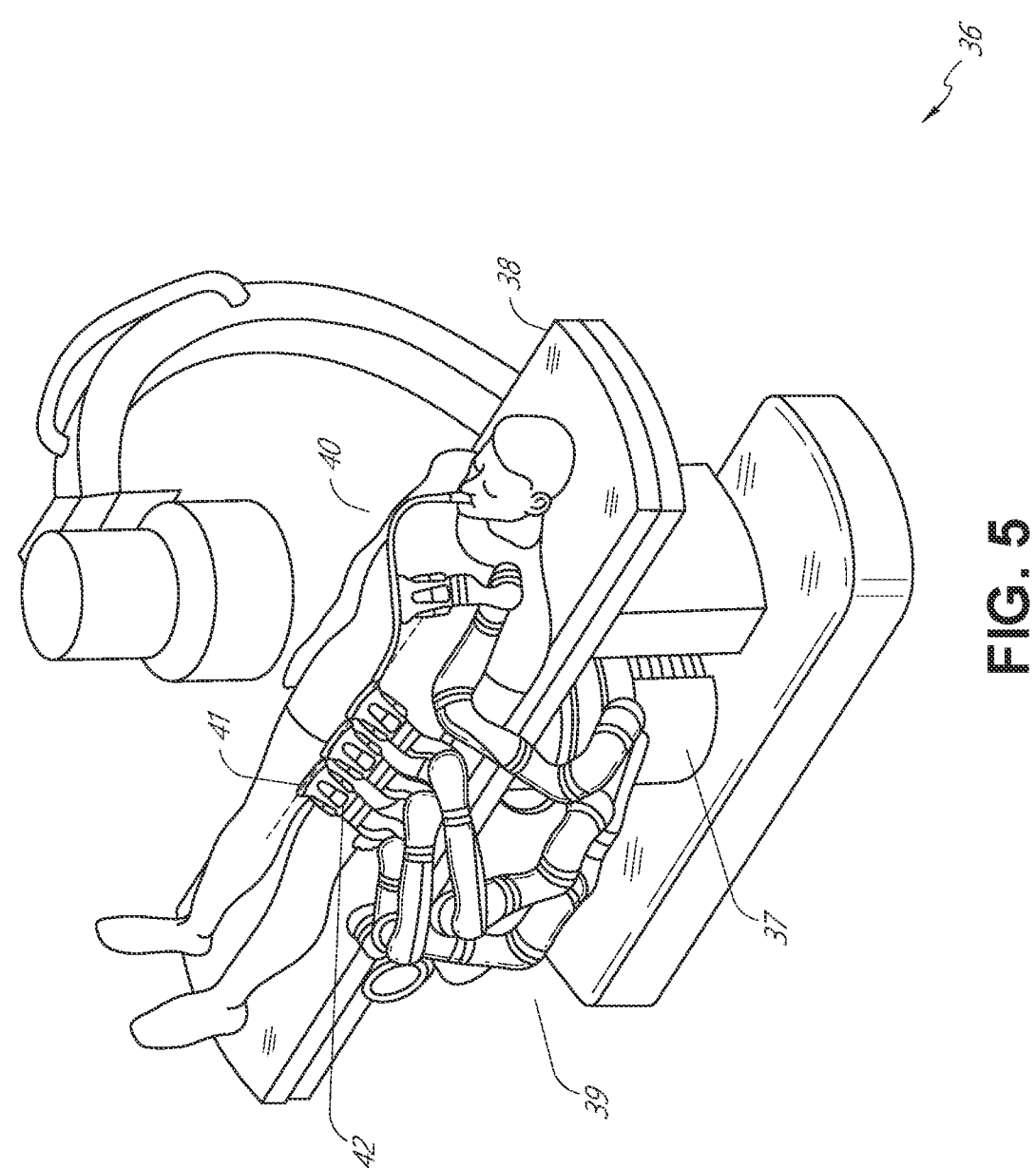
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
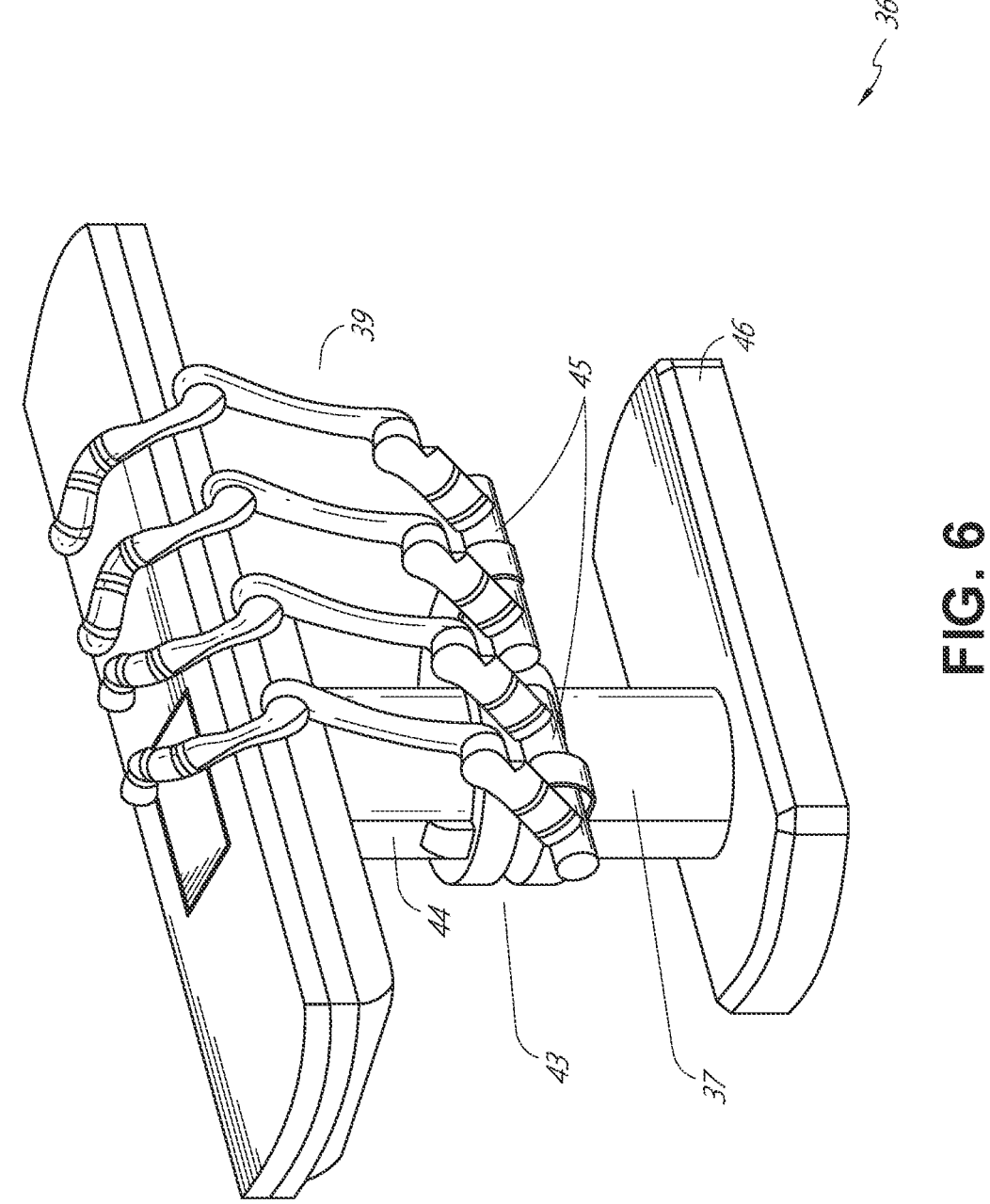
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
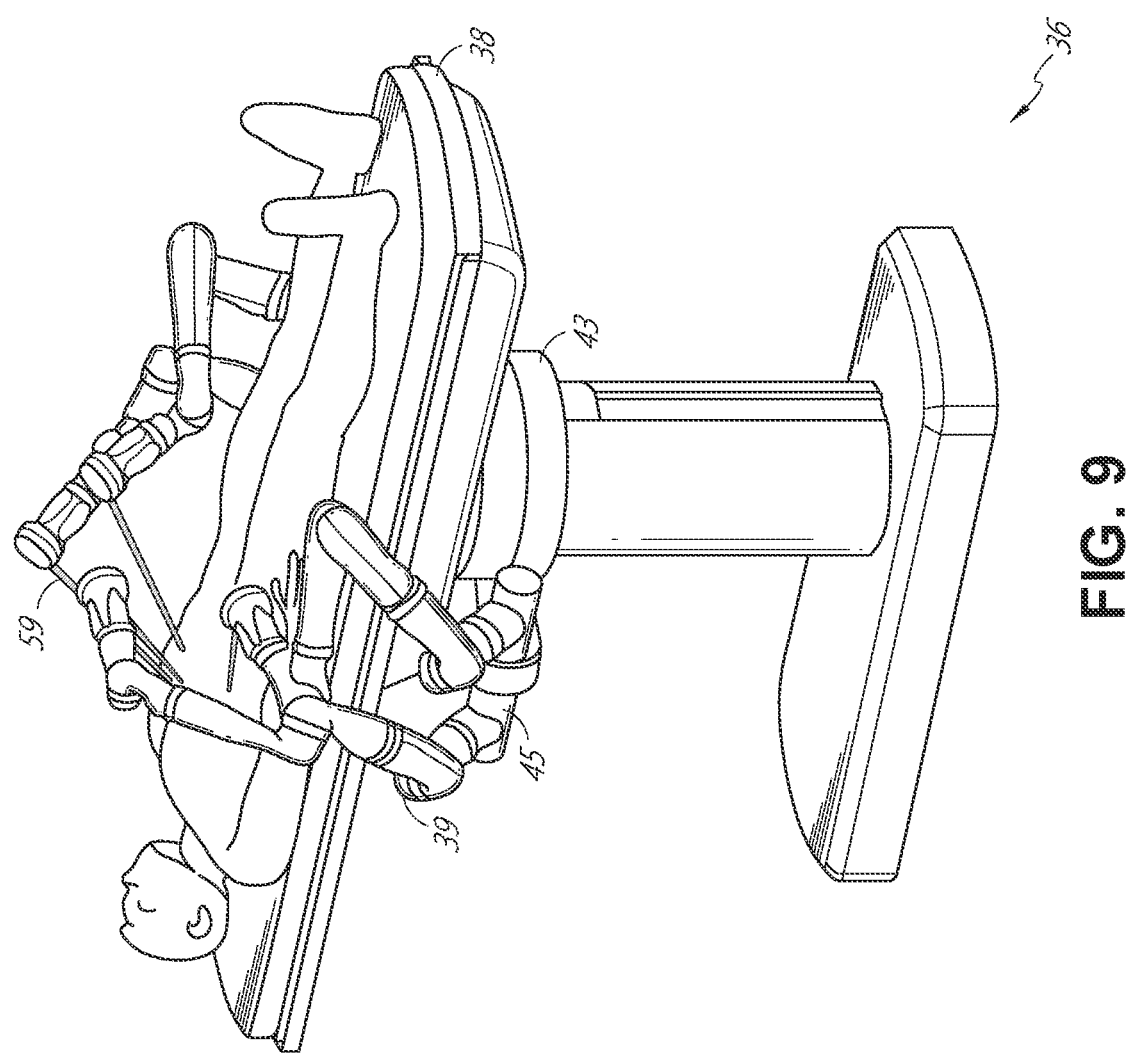
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
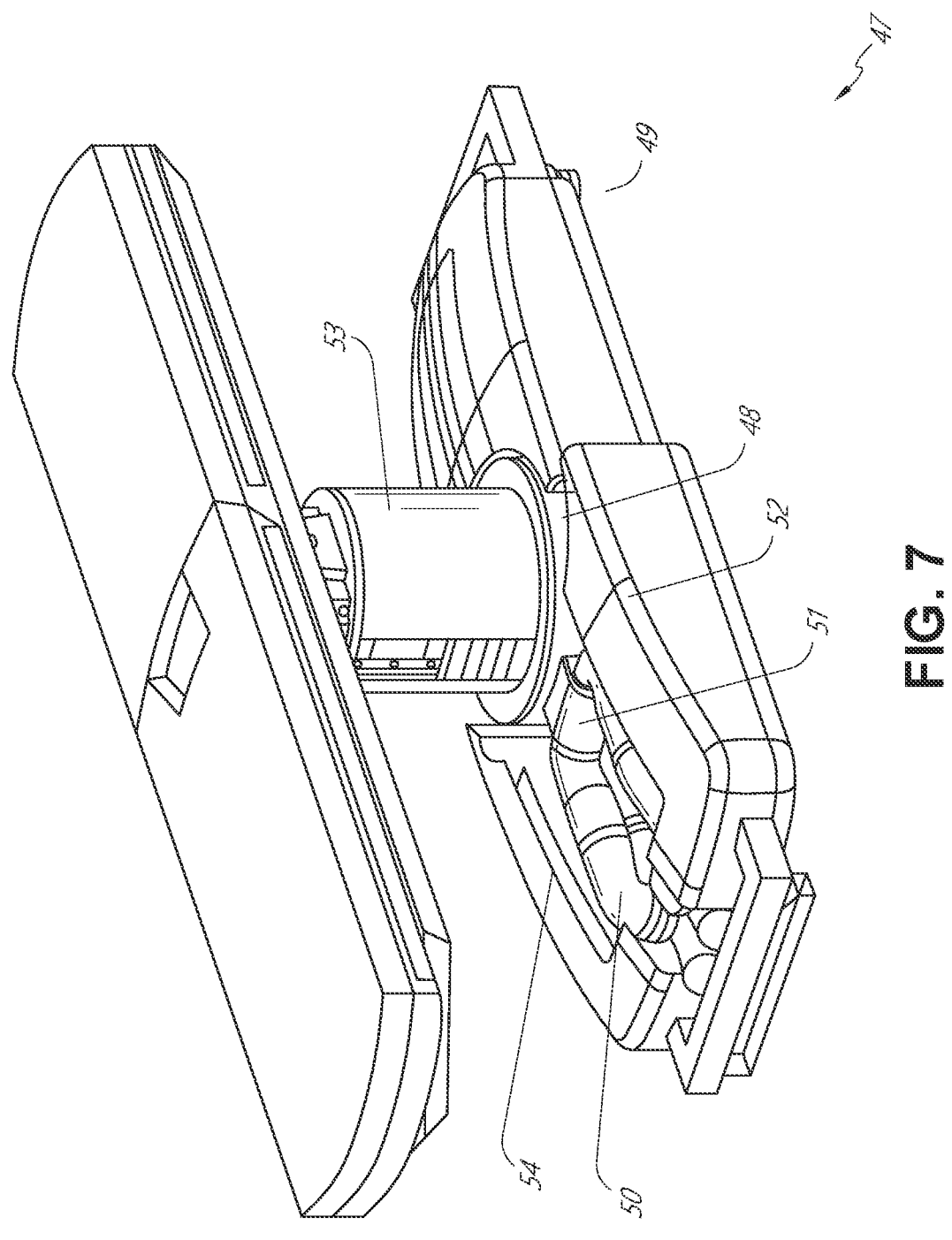
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
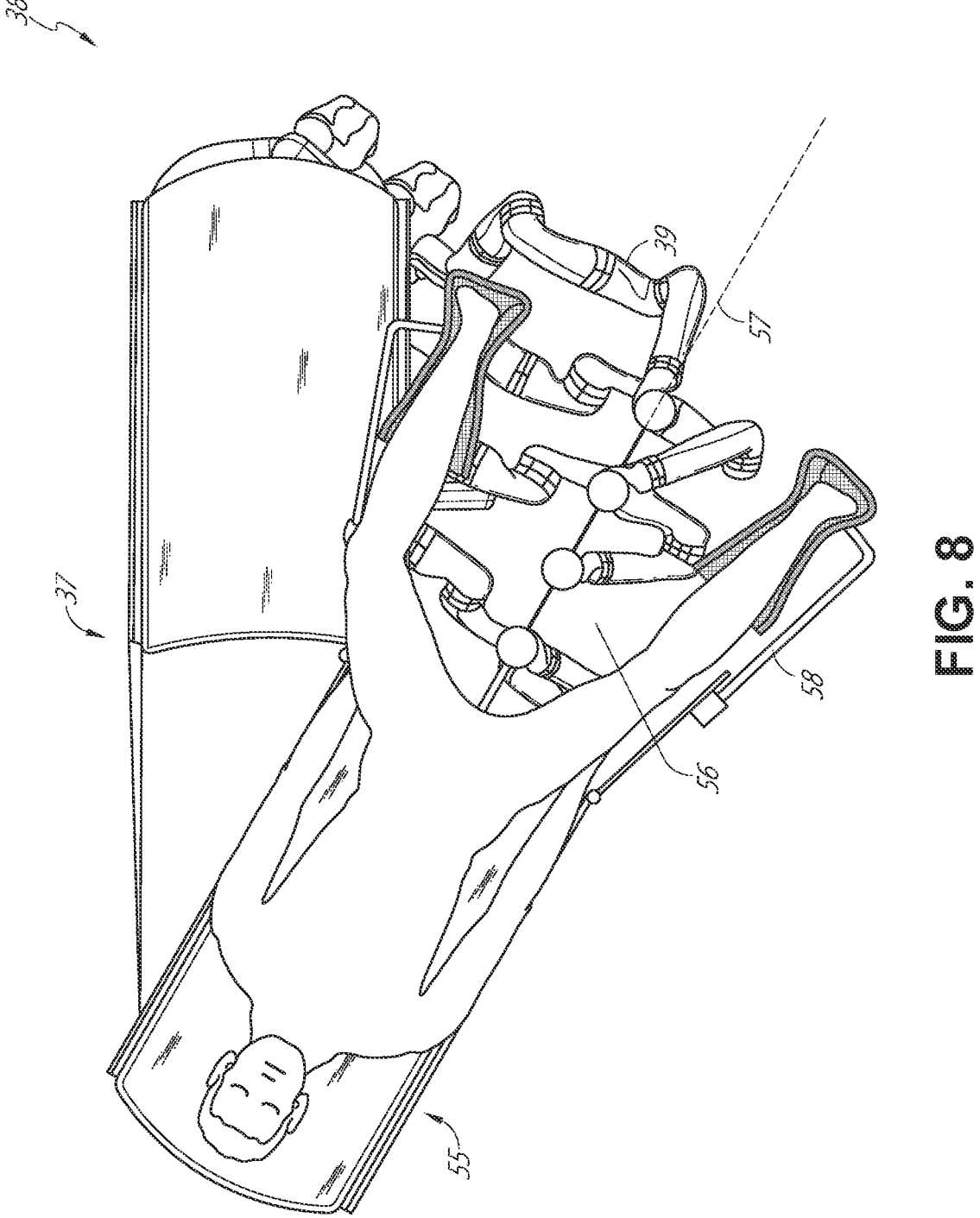
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
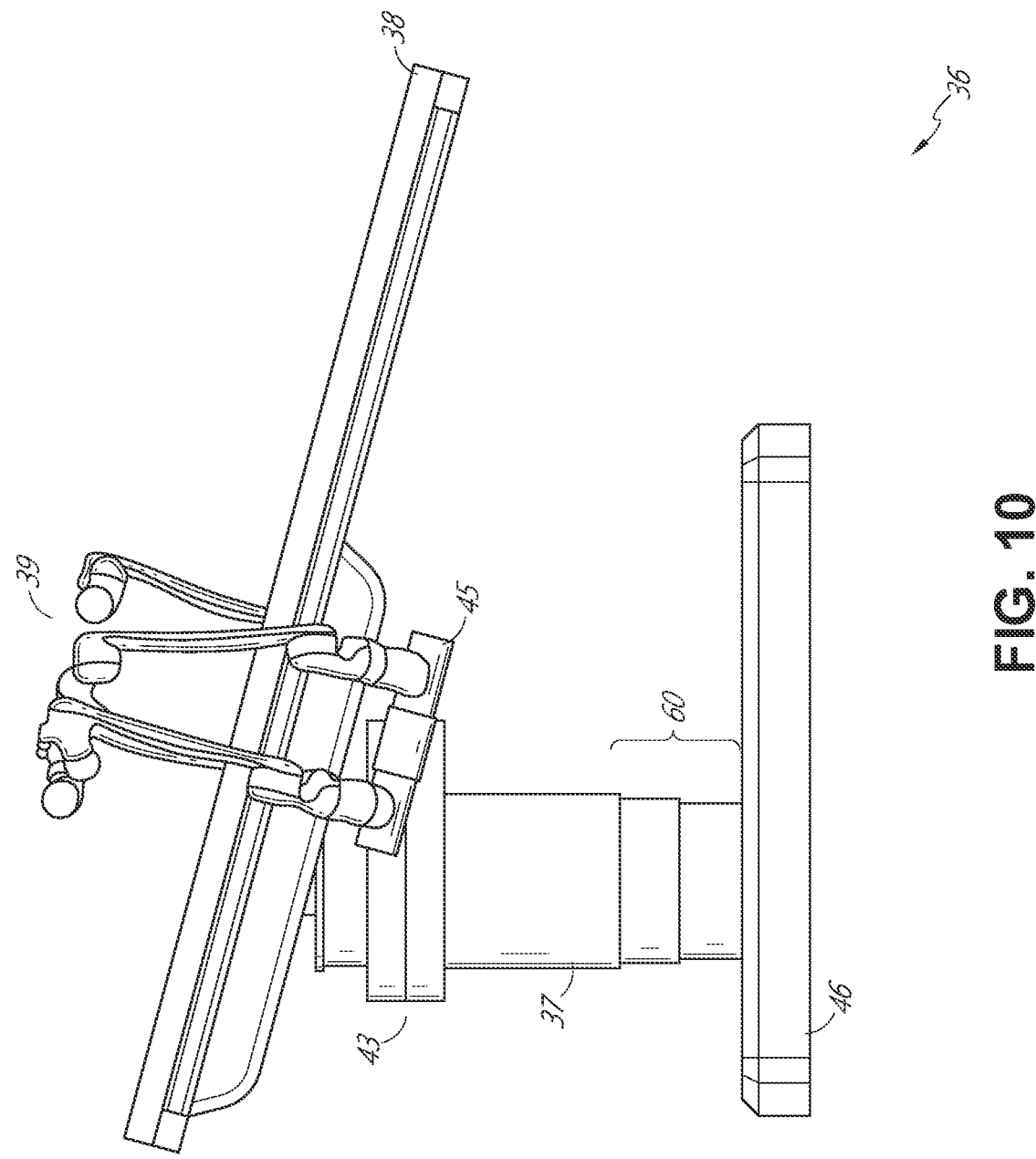
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
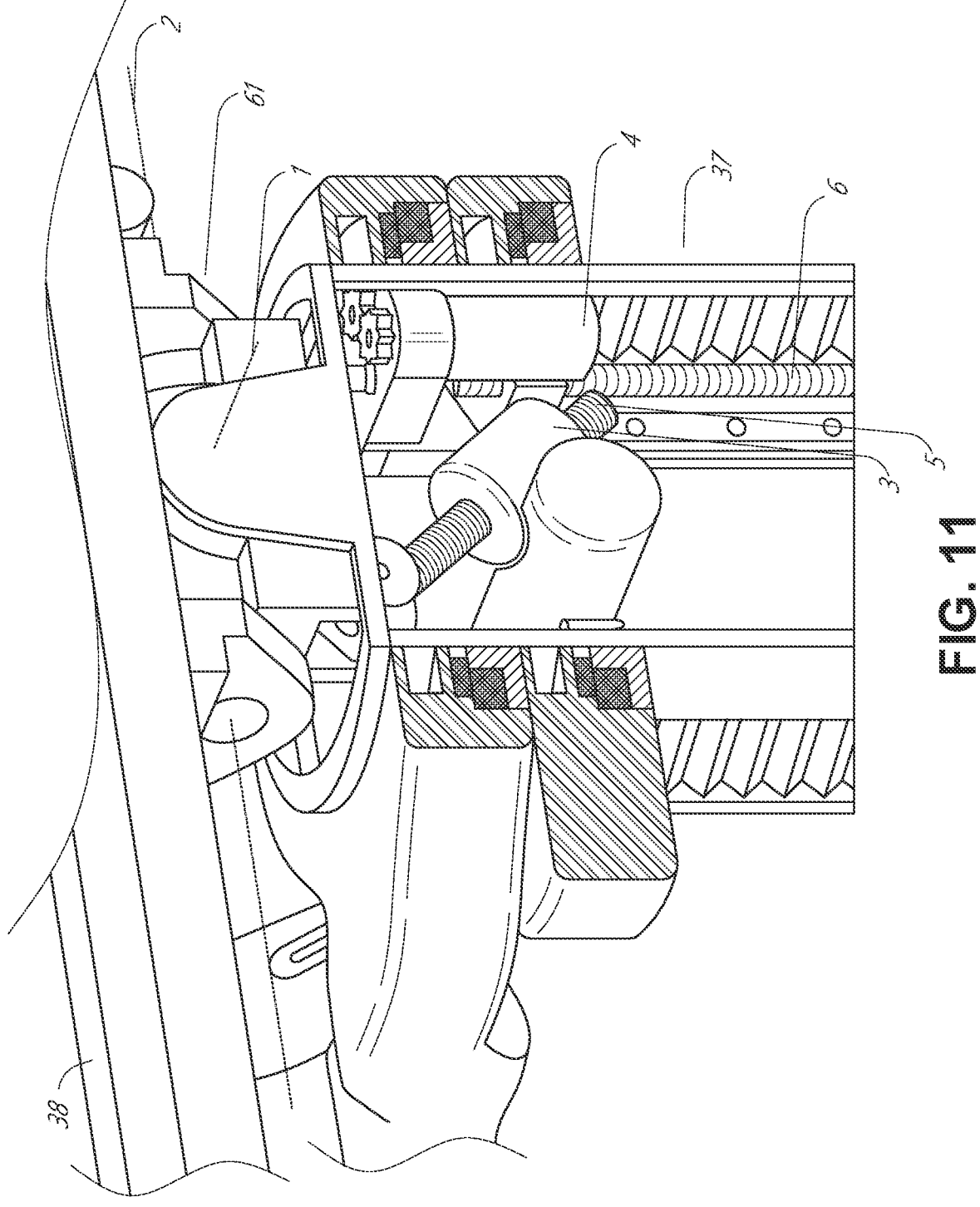
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
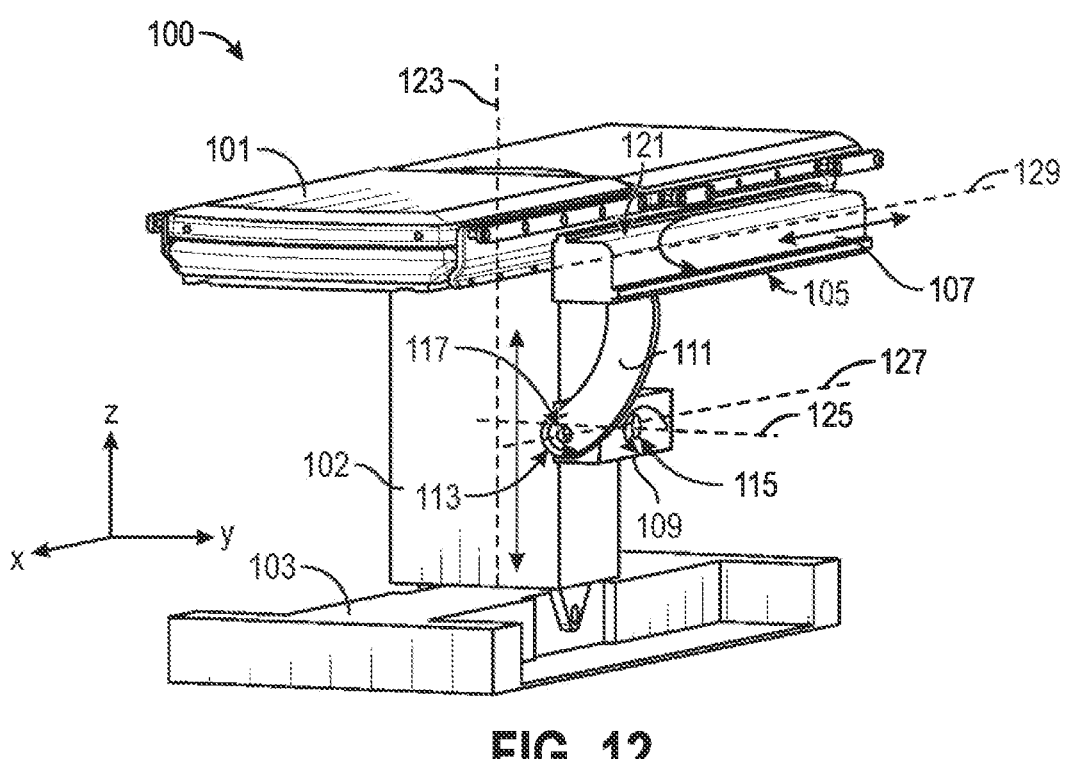
FIG. 12 illustrates an alternative embodiment of a table-based robotic system.
Figure 13:
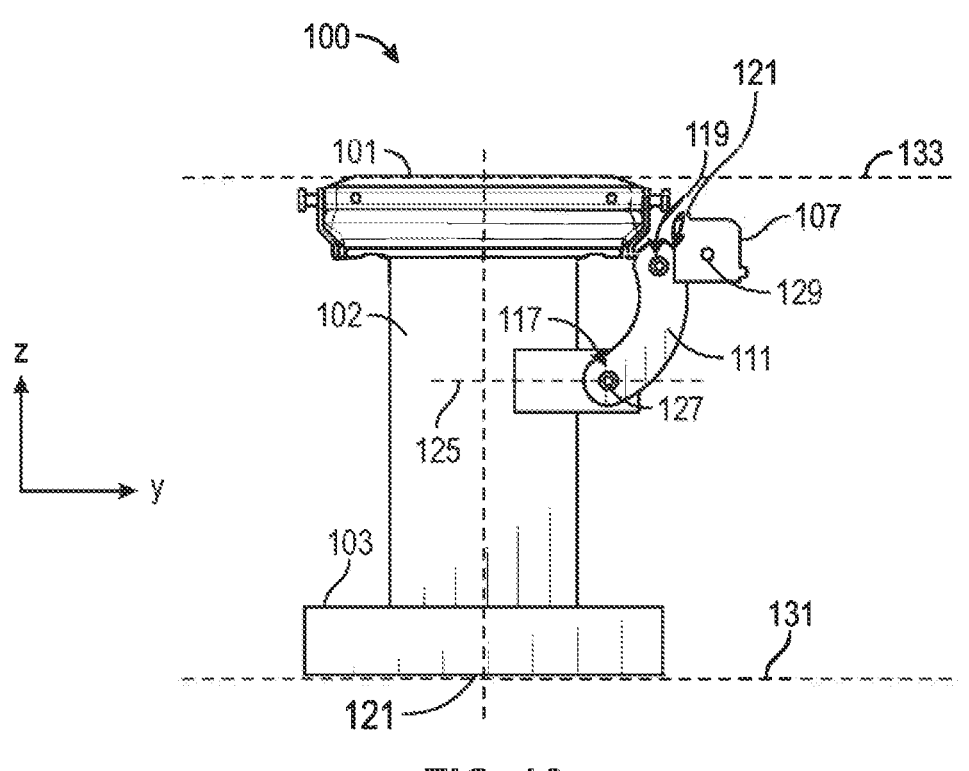
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG.

14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
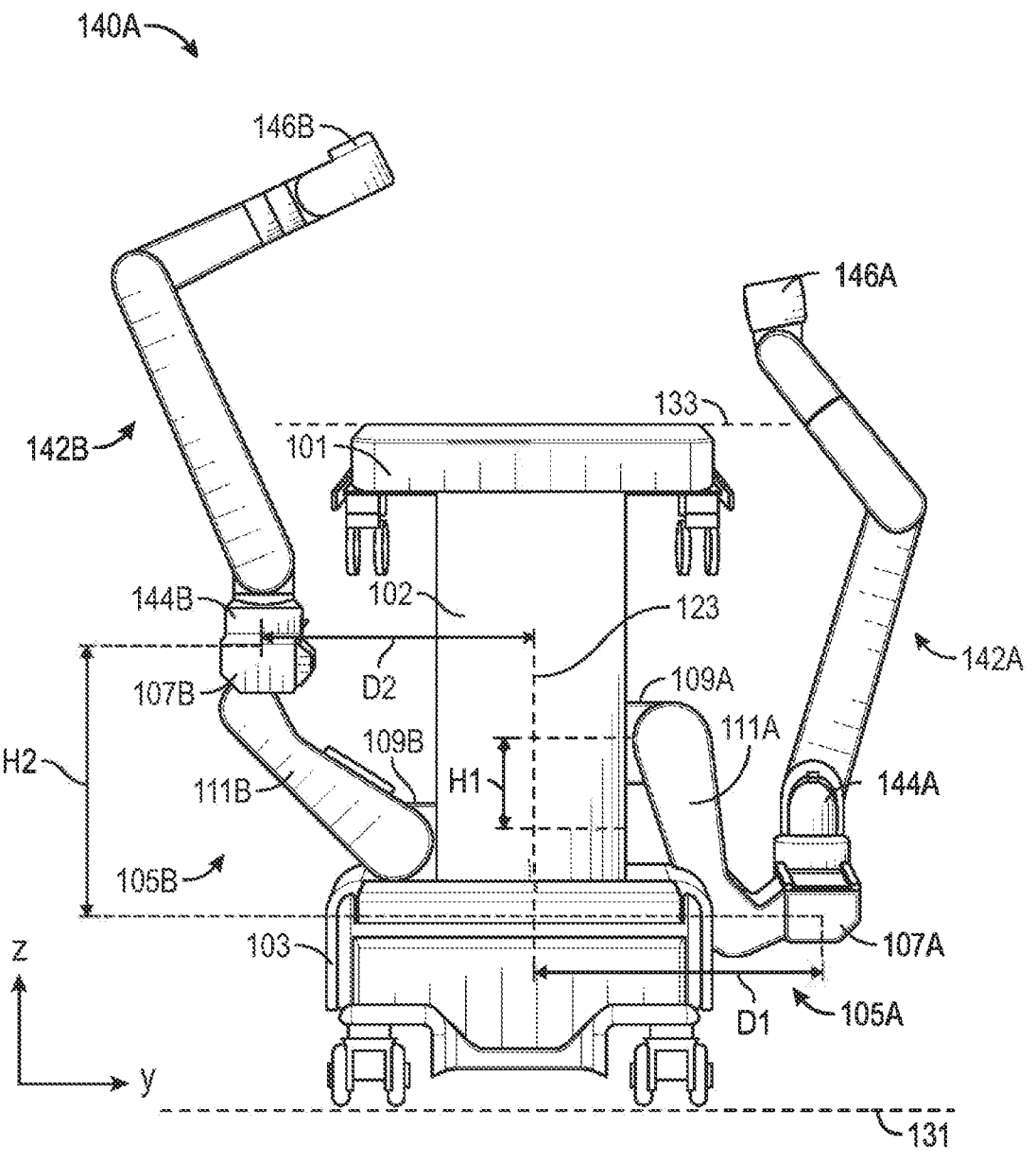
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (one degree of freedom, including insertion), a wrist (three degrees of freedom, including wrist pitch, yaw, and roll), an elbow (one degree of freedom, including elbow pitch), a shoulder (two degrees of freedom, including shoulder pitch and yaw), and base 144A, 144B (one degree of freedom, including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
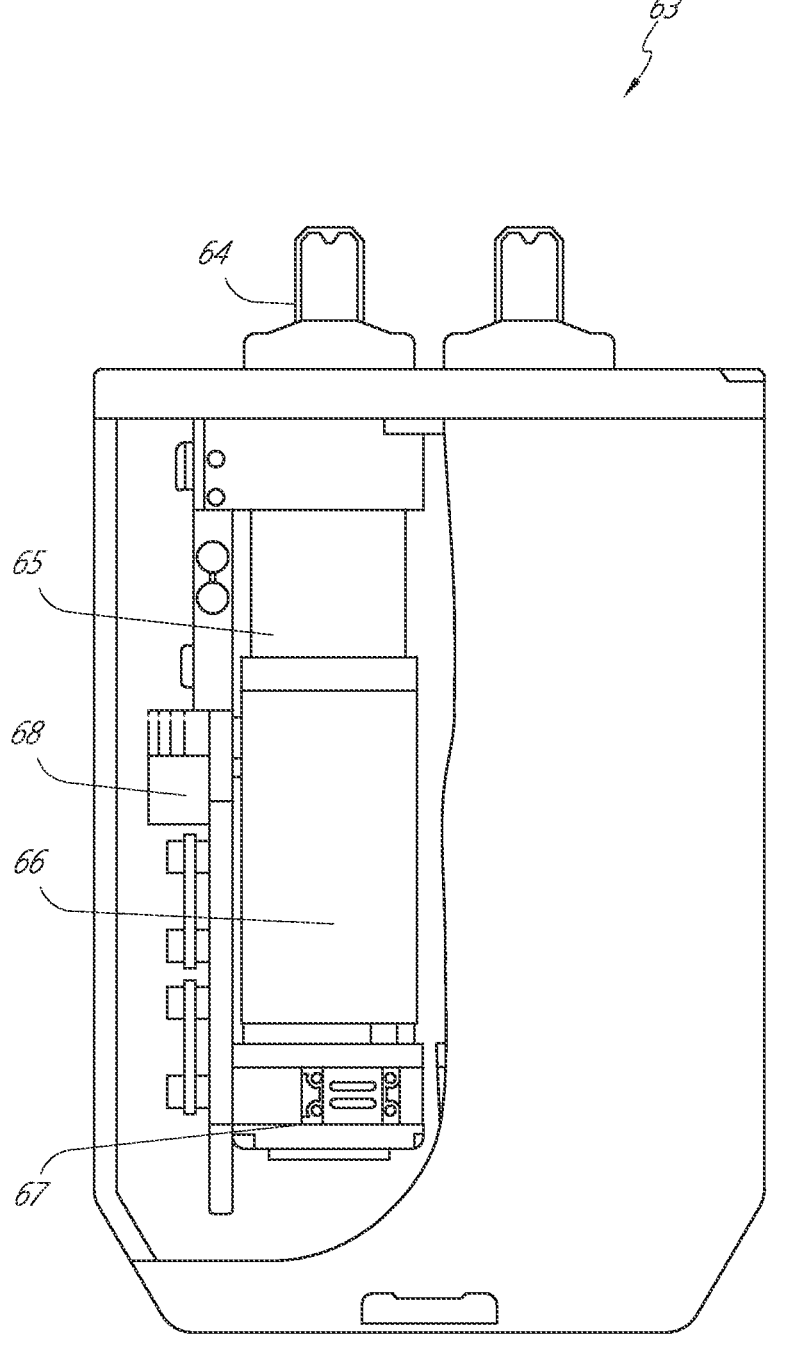
FIG. 15 illustrates an exemplary instrument driver.
Figure 15:

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
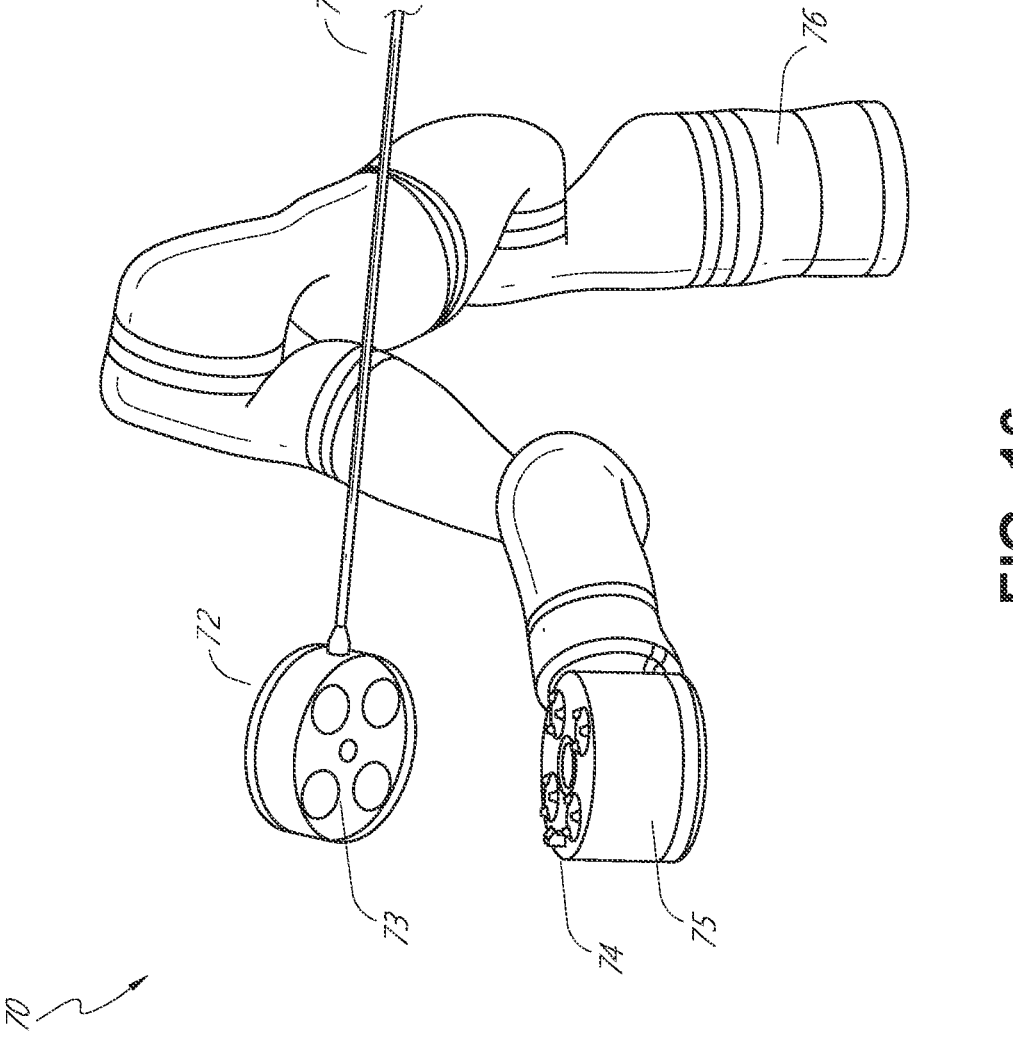
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
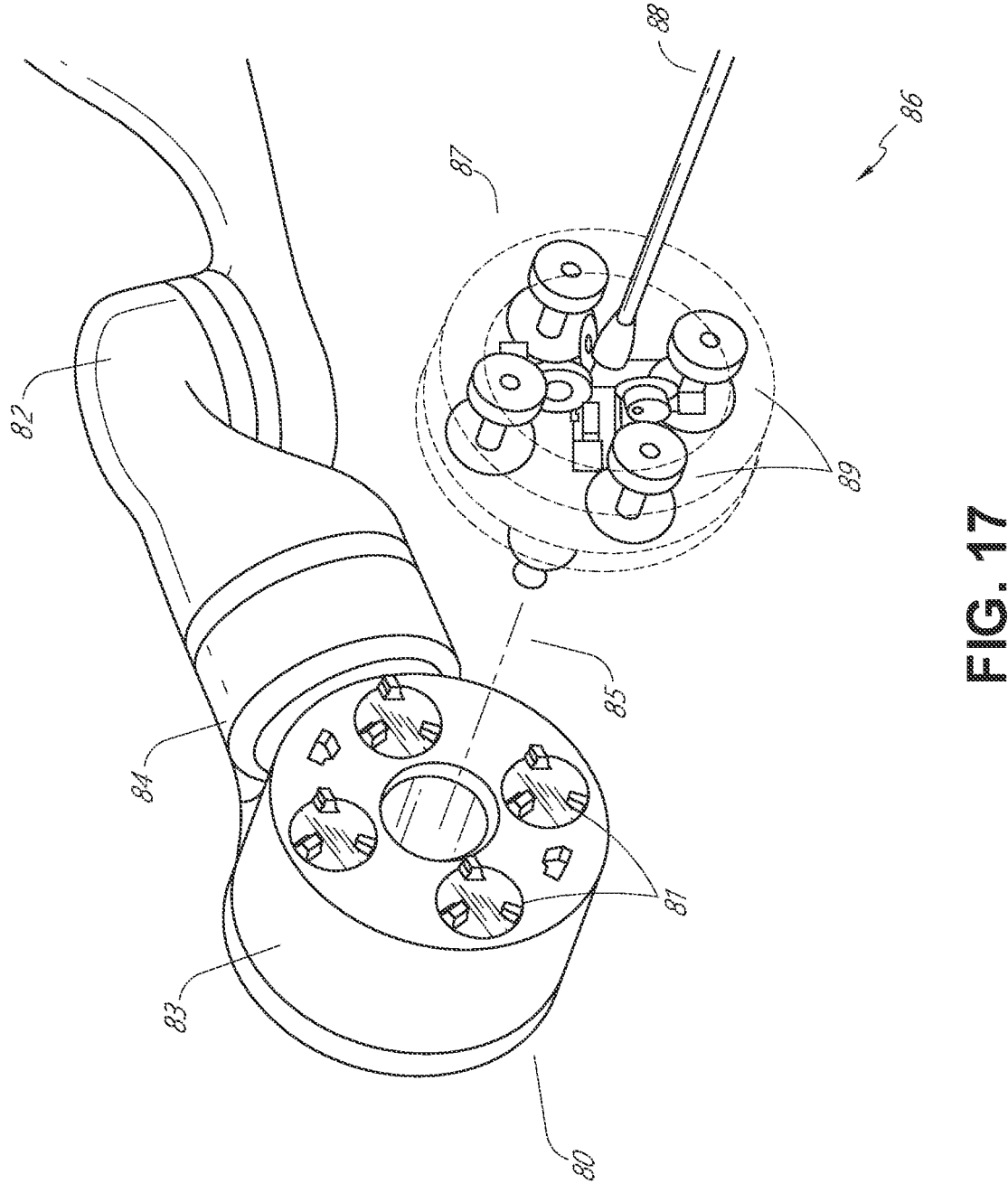
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
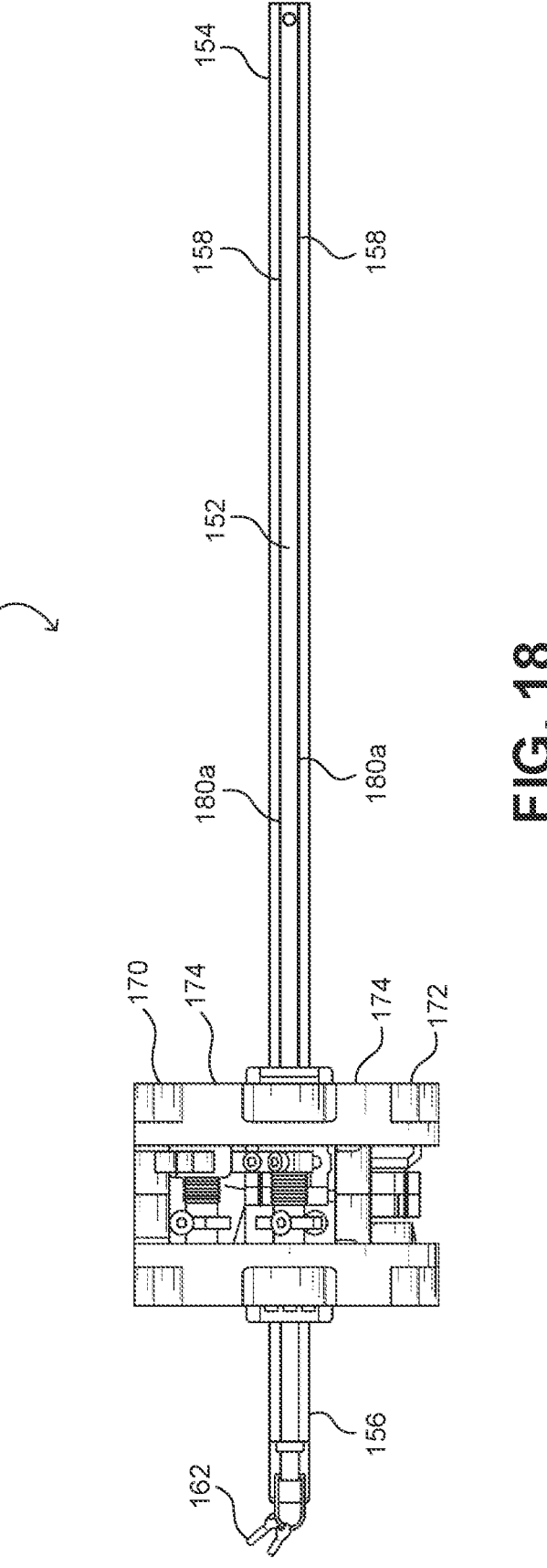
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
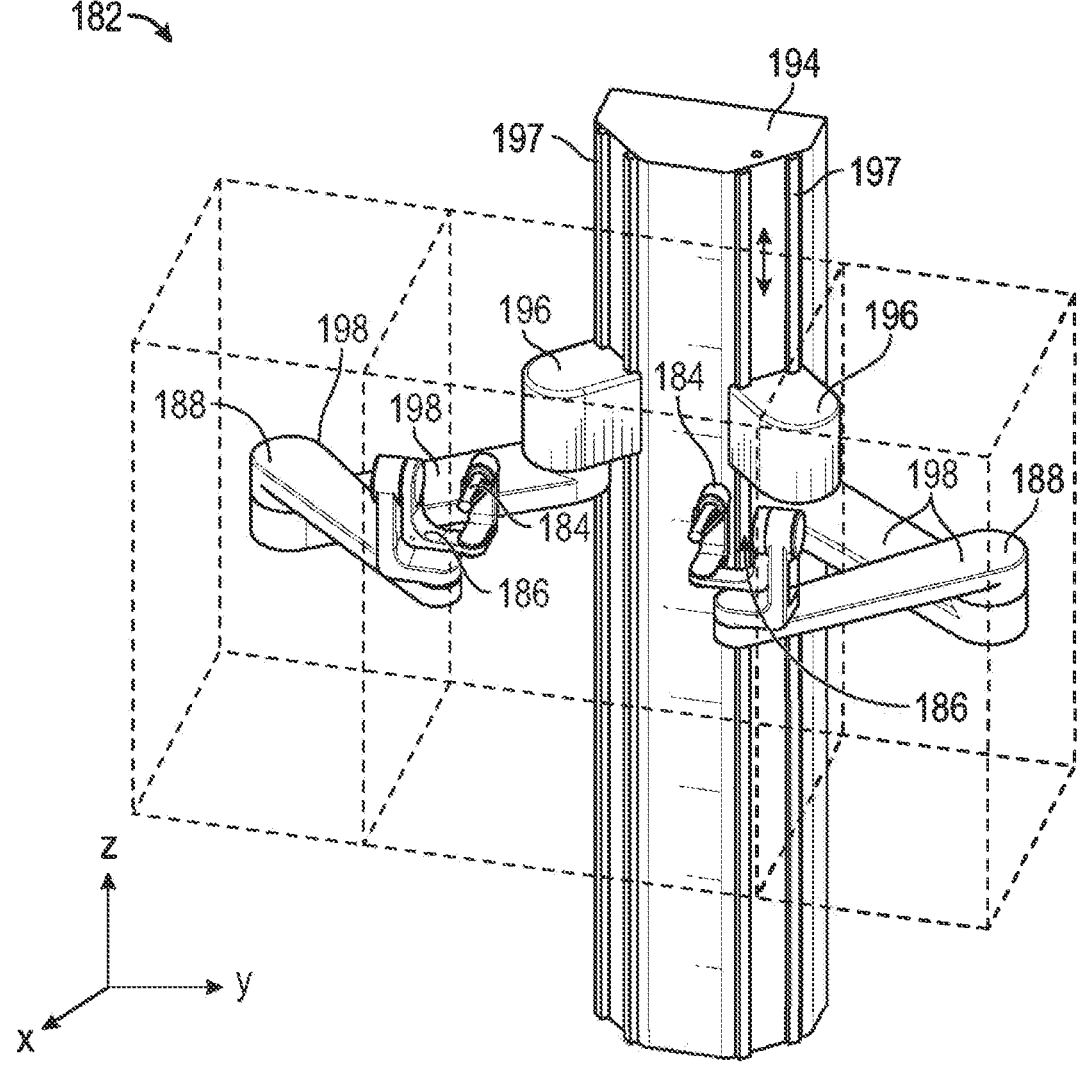
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
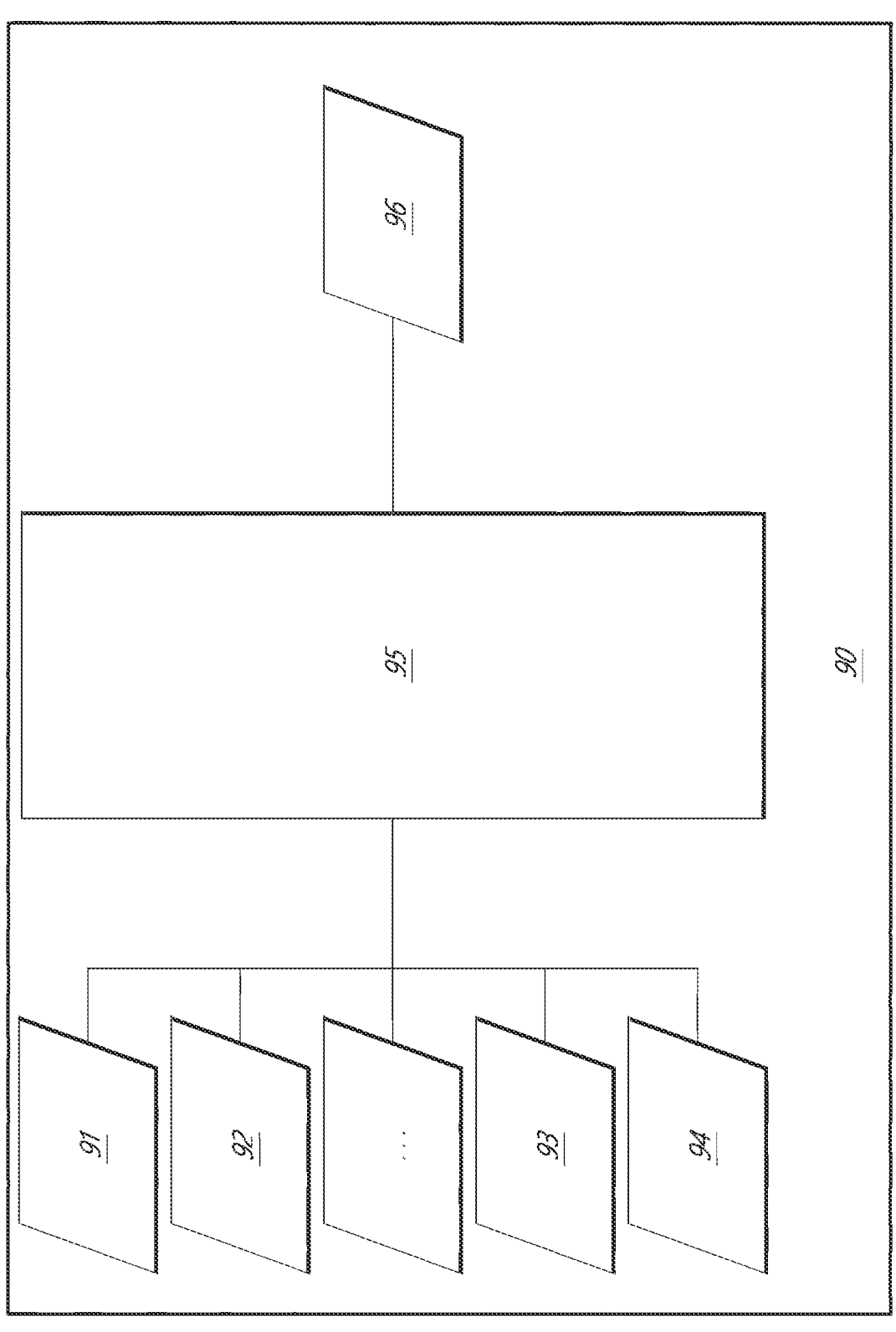
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Surgical Instruments

As described above, certain conventional laparoscopes or other surgical instruments include a tool driver adapter to allow the instrument to interface with a robotic system and a separate user interface to allow a clinician to control functions of the surgical instrument and/or robotic system. Therefore, in certain applications, certain conventional laparoscopes or surgical instruments may be longer than instruments configured to manual use. In some applications, certain laparoscopes or other surgical instruments that are relatively longer may be unwieldy for a clinician to handle and may not fit into standardized trays or compartments for sterilization processes.

Therefore, it may be desirable to reduce the overall length of the laparoscope or surgical instrument while maintaining the operational length of the instrument shaft, to allow for case of handling and permit sterilization using standardized processes. In accordance with some embodiments described herein, by removing the additional length of a separate user interface attached to an end of the instrument shaft, the overall length of the surgical instrument can be shortened without reducing the operational length of the instrument. In accordance with some embodiments described herein, the user interface can be combined with the tool drive adapter, eliminating the separate user interface, reducing overall instrument length while maintaining a desired operational or shaft length.

However, in certain applications, it may be challenging to accurately detect user inputs (e.g. button presses) when the user interface is moved to or combined with the tool drive adapter. In certain applications, since the tool drive adapter is configured to withstand sterilization procedures, certain conventional electronic arrangements for detecting user inputs may not be suitable for use within the tool drive adapter. For example, certain conventional electronic arrangements for detecting user inputs may not withstand sterilization procedures or function across sealed or isolated portions of the tool drive adapter.

Therefore, in accordance with certain embodiments described herein, it may be desired to utilize components, such as buttons or other user inputs, that can withstand sterilization and place electrical components for detecting user inputs (e.g. button presses) within a sealed compartment, such as the sealed instrument shaft. In certain applications, since the instrument shaft can rotate relative to the tool drive adapter and the buttons (or other user inputs), it may be challenging to reliably detect user inputs (e.g. state of the buttons on the tool drive adapter), as the instrument shaft rotates.

Advantageously, embodiments described herein address the challenges described herein and provide a laparoscope or other surgical instrument for use with a robotic system that provides a reduced overall length, while maintaining a desired operational length, while allowing for reliable detection of user inputs.

Figure 21:
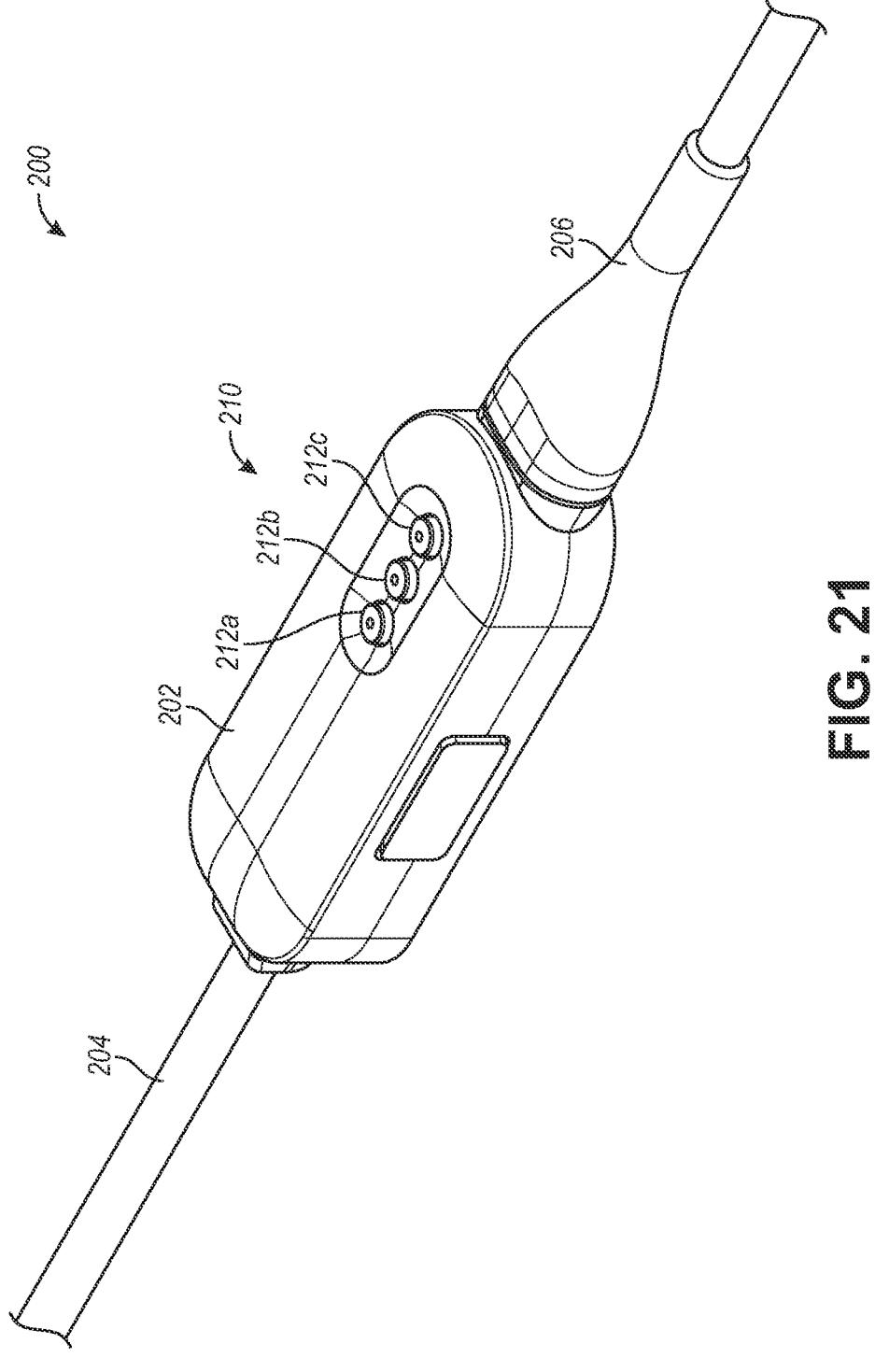
FIG. 21 illustrates a partial perspective view of a laparoscope, in accordance with some embodiments.

FIG. 21 illustrates a partial perspective view of a laparoscope 200, in accordance with some embodiments. As described herein, a laparoscope 200 facilitates therapeutic interventions by providing an view of an internal surgical site during a surgical procedure. In the depicted example, the laparoscope 200 includes a camera or other suitable optical device to view a site disposed at the end of the instrument shaft 204. During operation, the instrument shaft 204 can be advanced, manipulated, and/or rotated to position the camera and instrument shaft 204 in a desired position relative to the patient. In some embodiments, the laparoscope 200 may include surgical tools or instruments to perform a surgical procedure. Optionally, the instrument shaft 204 can be manipulated or rotated to perform a surgical procedure. The instrument shaft 204 may be formed at least partially from stainless steel.

In some embodiments, the laparoscope 200 can be coupled to a robotic surgical system, such as the systems described herein, by attaching the tool drive adapter 210 to a mating portion of the robotic surgical system. As illustrated, the housing 202 of the tool drive adapter 210 can be configured to mate with a complementary portion of the robotic surgical system. During operation, the instrument shaft 204 may rotate relative to the tool drive adapter 210 and the robotic surgical system.

In the depicted example, the laparoscope 200 can include one or more user interface elements or buttons 212a, 212b, 212c to allow a clinician to control the operation of the laparoscope and/or functions of the attached robotic system. During operation, electronic components of the laparoscope 200 can detect when a button 212a, 212b, 212c is pressed or released and provide a corresponding signal to other portions of the laparoscope 200 or the connected robotic system. Optionally, the laparoscope 200 can include more or fewer user interface elements or buttons.

As illustrated, the user interface elements or buttons 212a, 212b, 212c can be disposed on or otherwise integrated with the housing 202 of the tool drive adapter 210. In some applications, by combining or integrating the buttons 212a, 212b, 212c with the tool drive adapter 210, embodiments of the laparoscope 200 may eliminate the need for a separate user interface portion attached to the end of the instrument shaft 204, reducing the overall length of the laparoscope 200, while maintaining the effective operational length of the instrument shaft 204. Advantageously, by reducing the overall length of the laparoscope 200 compared to certain conventional laparoscopes, the laparoscope 200 may be easier to handle and allow for sterilization using standardized procedures.

In some embodiments, signals from the buttons 212a, 212b, 212c can be provided to portions of the laparoscope 200 and/or the robotic system via a connector 206. In some embodiments, video signals and/or control signals can be sent to or from the laparoscope 200 via the connector 206.

Figure 22:
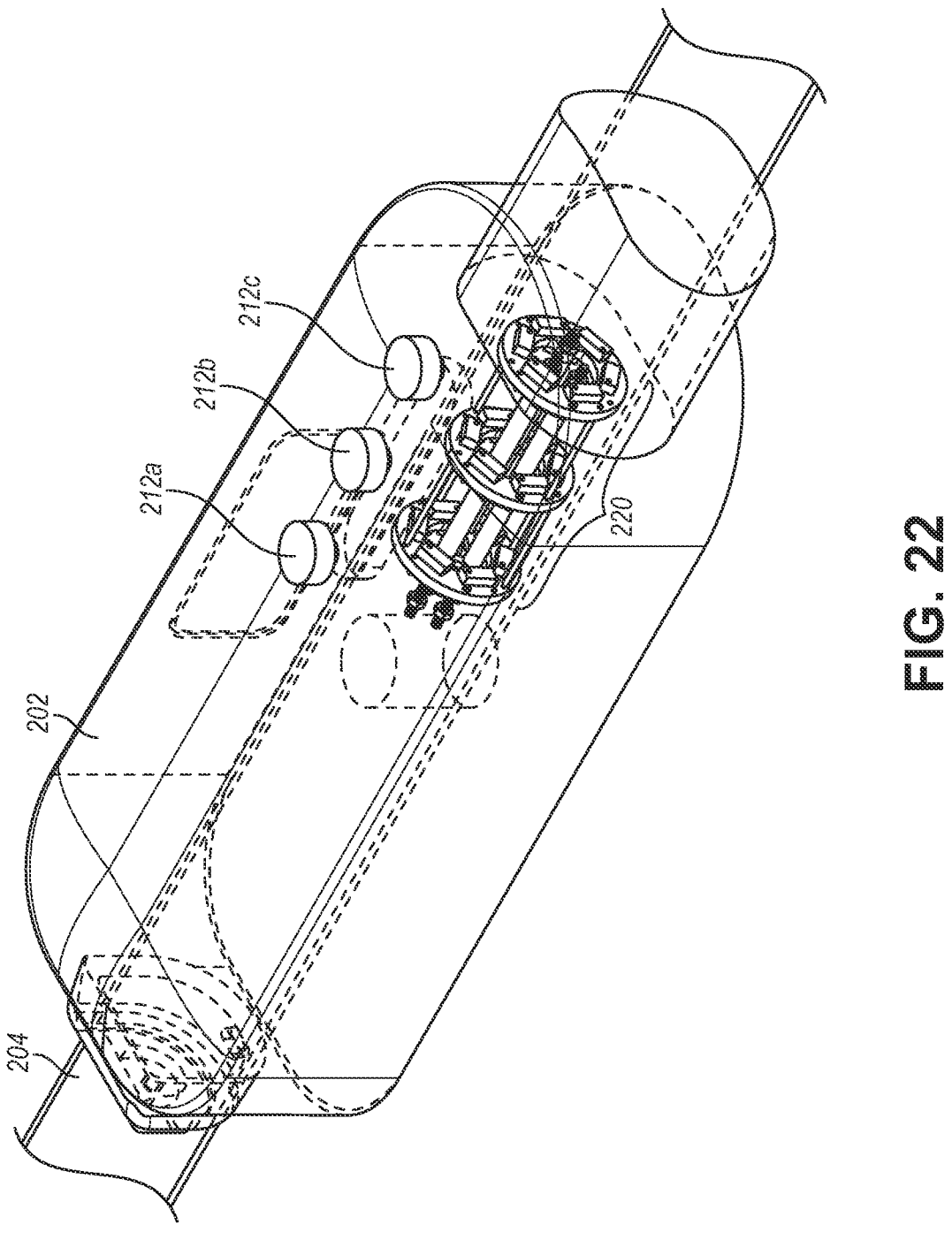
FIG. 22 illustrates a partial perspective view of the laparoscope of FIG. 21 with a housing shown in hidden lines.
Figure 23:
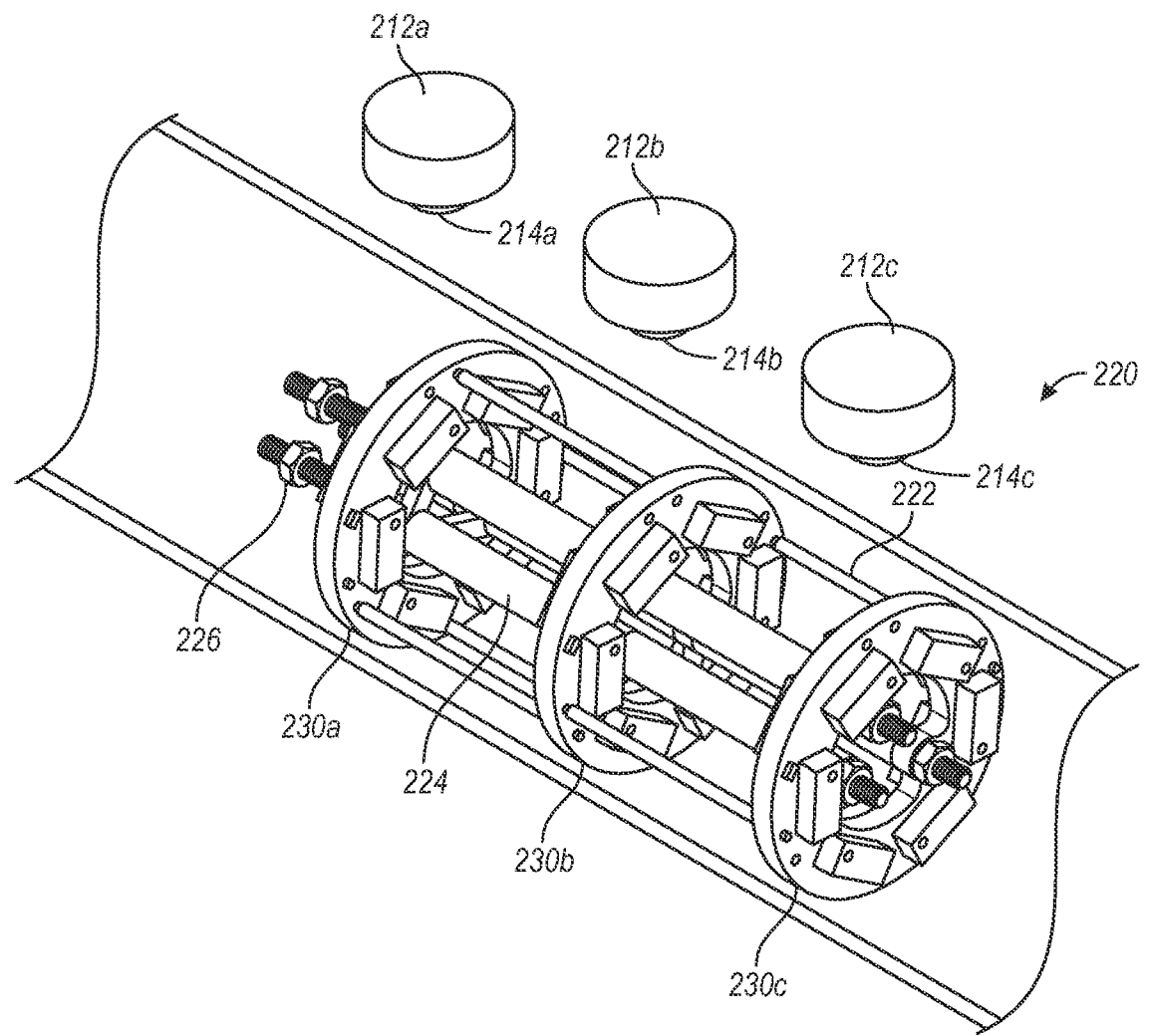
FIG. 23 illustrates a perspective view of a sensor array of the laparoscope of FIG. 21.

FIG. 22 illustrates a partial perspective view of the laparoscope 200 of FIG. 21 with a housing 202 shown in hidden lines. FIG. 23 illustrates a perspective view of a sensor array 220 of the laparoscope of FIG. 21. With reference to FIGS. 22 and 23, as illustrated, the laparoscope 200 includes a sensor array 220 to detect the position or state of one or more buttons 212a, 212b, 212c.

In the depicted example, the sensor array 220 can wirelessly detect the position, actuation, or state of the buttons 212a, 212b, 212c. In some embodiments, the sensor array 220 can detect changes in magnetic field to determine the state of the buttons 212a, 212b, 212c. In the depicted example, the buttons 212a, 212b, 212c can include or be coupled to magnetic elements 214a, 214b, 214c such that the magnetic field experienced by the sensor array 220 changes as the buttons 212a, 212b, 212c are pressed, released, or otherwise actuated. Advantageously, since the buttons 212a, 212b, 212c do not contain any active electronic elements (i.e. passive elements), the buttons 212a, 212b, 212c can withstand sterilization processes, allowing the tool drive adapter 210 to be sterilized. In certain applications, certain conventional electronic or active user interface elements may not withstand sterilization procedures.

In the depicted example, the sensor array 220 includes one or more array components 230a, 230b, 230c to detect the actuation or change of state of a respective button 212a, 212b, 212c by detecting the change in magnetic field of the respective magnetic elements 214a, 214b, 214c. As illustrated, each array component 230a, 230b, 230c can be aligned with a respective magnetic element 214a, 214b, 214c to detect the state of the respective button 212a, 212b, 212c. For example, each array component 230a, 230b, 230c can be aligned along the axis of rotation of the instrument shaft 204 with a respective magnetic element 214a, 214b, 214c to detect the state of the button 212a, 212b, 212c. Optionally, the sensor array can include more or fewer array components corresponding to the number of user interface elements or buttons.

Optionally, the array components 230a, 230b, 230c can be coupled together to maintain alignment between the array components 230a, 230b 230c and the respective magnetic elements 214a, 214b, 214c and/or between the other array components. For example, the array components 230a, 230b, 230c can be coupled together with bolts or shafts 224 and secured with fasteners 226. In some embodiments, the array components 230a, 230b, 230c can be electrically coupled together via connectors or wires 222.

As illustrated, the sensor array 220 is disposed within the instrument shaft 204. In some embodiments, the sensor array 220 is sealed, isolated, or otherwise enclosed within the instrument shaft 204 without compromising the integrity or otherwise breaching the instrument shaft 204. Advantageously, since the components of the sensor array 220 are disposed or otherwise isolated within the instrument shaft 204, sensitive electronic components are protected from certain conditions that may be present during sterilization procedures, allowing the instrument shaft 204 to be sterilized. As described herein, certain conventional electronic components or arrangements for detecting user inputs may not withstand sterilization procedures or function across sealed or isolated portions of the tool drive adapter.

In the depicted example, the sensor array 220 can rotate with the instrument shaft 204, permitting the sensor array 220 to rotate relative to the housing 202 and the buttons 212a, 212b, 212c. As described herein, embodiments of the sensor array 220 can detect changes in magnetic field to determine the state of the buttons 212a, 212b, 212c as the sensor array 220 rotates relative to the buttons 212a, 212b, 212c.

Figure 24:
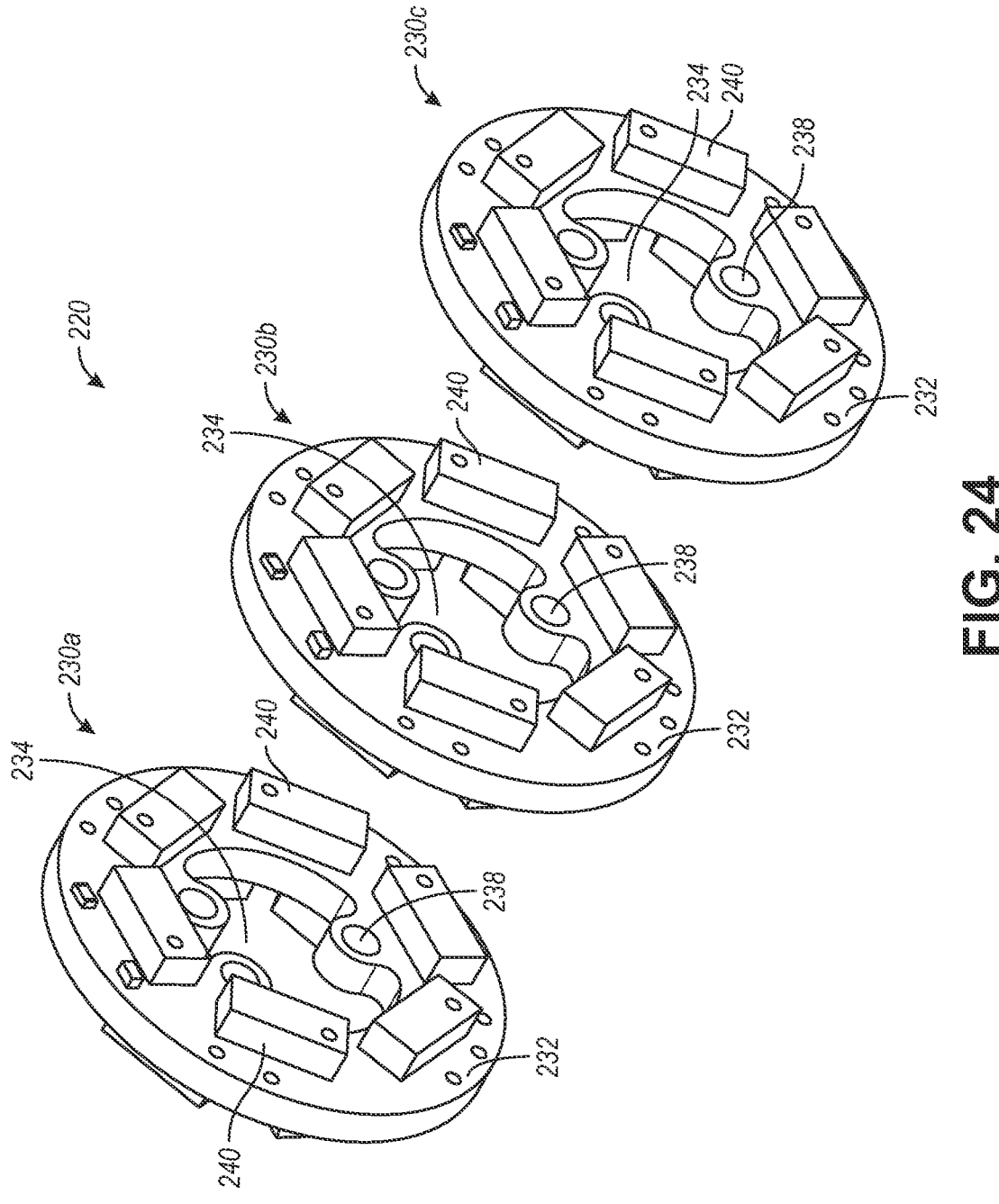
FIG. 24 illustrates a partial exploded view of the sensor array of FIG. 23.
Figure 25:
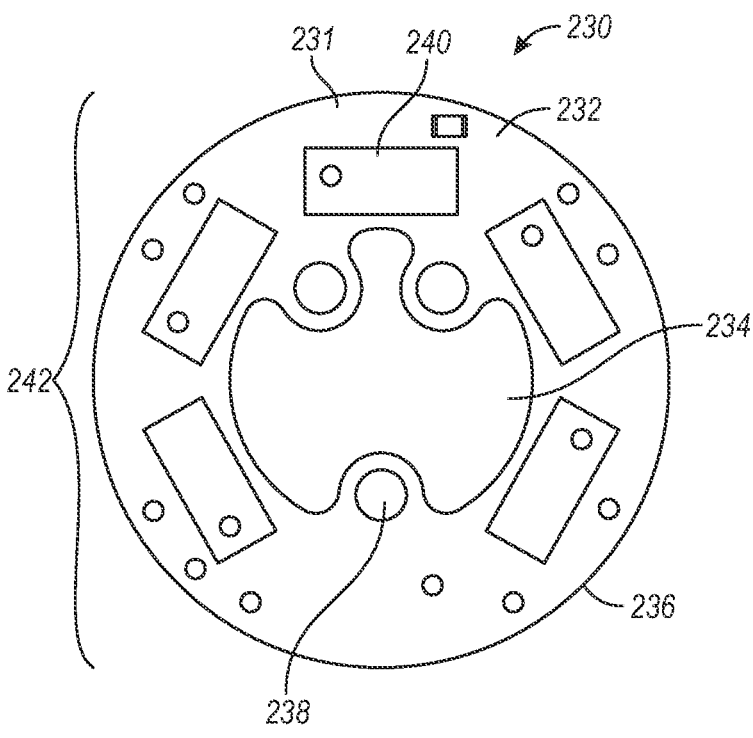
FIG. 25 illustrates a front elevation view of an array component of the sensor array of FIG. 23.
Figure 26:
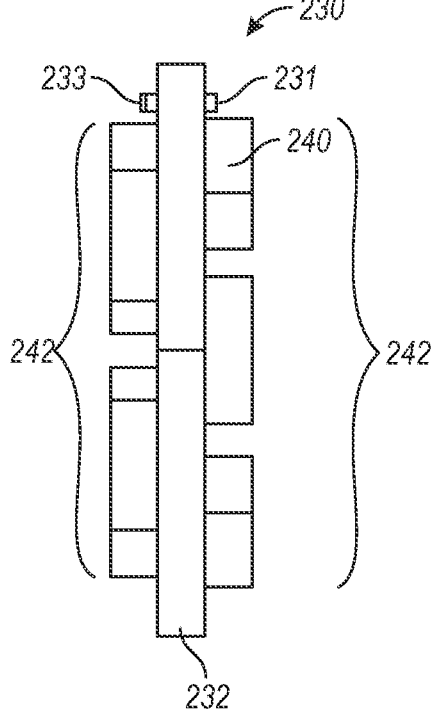
FIG. 26 illustrates a side elevation view of the array component of FIG. 25.

FIG. 24 illustrates a partial exploded view of the sensor array 220 of FIG. 23. FIG. 25 illustrates a front elevation view of an array component 230 of the sensor array 220 of FIG. 23. FIG. 26 illustrates a side elevation view of the array component 230 of FIG. 25. With reference to FIGS. 24-26, in some embodiments, each array component 230*a*, 230*b*, 230*c*, generally referred to as array component 230, includes one or more sensor 240 to detect a state of a respective button 212*a*, 212*b*, 212*c*. In some embodiments, the sensors 240 may include reed switches, hall effect sensors, and/or capacitive touch sensors.

In the depicted example, the array component 230 can include one or more sensors 240 to detect a change in magnetic field of a magnetic element (e.g. magnetic elements 214*a*, 214*b* 214*c*, generally referred to as magnetic element 214) to detect the position of a user input or button (e.g. buttons 212*a*, 212*b*, 212*c*, generally referred to as button 212). During operation, one or more sensors 240 can change in state (e.g. from an open state to a closed state) in response to a user input or button 212 press to provide a corresponding signal to the laparoscope 200 or the connected robotic system. For example, one or more sensors 240 may change from an open state to a closed state when a corresponding button 212 is pressed, and may change from a closed state to an open state when the corresponding button 212 is released. In some applications, an open state may correspond to an open circuit and a closed state may correspond to a closed circuit.

In some embodiments, the sensors 240 can be reed switches that are configured to move between a first state, such as an open state (i.e. open circuit) and a second state, such as a closed state (i. e. closed circuit), in response to an applied magnetic field or magnetomotive force. In some embodiments, the reed switch sensor 240 may have a magnetomotive force threshold wherein the sensor 240 moves from an open state to a closed state in response to the magnetomotive force experienced by the sensor 240. For example, a reed switch sensor 240 can move or change to a closed state when the button 212 and the corresponding magnetic element 214 are pressed or actuated, such that the magnetic element 214 provides sufficient magnetic field or magnetomotive force to actuate or affect the reed switch sensor 240 to a closed state or position. Further, the reed switch sensor 240 can be configured to be in an open state when a button 212 and corresponding magnetic element 214 is in a resting position, such that the magnetic element 214 does not provide sufficient magnetic field or magnetomotive force to actuate or affect the reed switch sensor 240 to the closed state or position. Advantageously, the use of reed switches does not require any standby power to detect a button press.

In some applications, the magnetomotive force threshold of the reed switch sensor 240 can be adjusted such that the sensor 240 is in an open state when the button 212 and the corresponding magnetic element 214 is in a resting position and the sensor 240 is in a closed state when the button 212 and the corresponding magnetic element 214 are in a depressed or actuated position. In some embodiments, the magnetomotive force threshold of the reed switch sensor 240 can be adjusted by altering or specifying parameters of the reed switch sensor 240. In some embodiments, the size or strength of the magnetic elements 214 can be configured to provide a magnetomotive force below the magnetomotive force threshold when the button 212 is in a resting position and above the magnetomotive force threshold when the button 212 is in the actuated position. In some embodiments, the spacing and/or orientation of the magnetic elements 214 and/or the sensor 240 can be adjusted or modified such that the effective magnetomotive force applied to the sensor 240 is below the magnetomotive force threshold when the button 212 is in the resting position and the effective magnetomotive force applied to the sensor 240 is above the magnetomotive force threshold when the button 212 is in the actuated position. In some embodiments, the sensor 240 may be placed in on its side, lengthwise, widthwise, rotated, and/or an inverted orientation relative to the printed circuit board 232.

In the depicted example, each array component 230 can include multiple sensors 240 in an arrangement 242 to allow the array component 230 to detect the state of a respective button 212 as the array components 230 of the sensor array 220 rotate with the instrument shaft 204 and relative to the respective button 212. In some embodiments, the sensors 240 of the array component 230 and/or a corresponding magnetic element 214 can be configured such that at least one sensor 240 accurately detects and indicates the state of the respective button 212 as the array components 230 of the sensor array 220 rotate with the instrument shaft 204 and relative to the respective button 212.

As illustrated, the array component 230 may include multiple sensors 240 in an arrangement 242, such that at least one sensor 240 adjacent to the magnetic element 214 during the course of rotation experiences sufficient magnetic field or magnetomotive force to exceed the magnetomotive force threshold of the sensor 240 and move or change to a closed state when the button 212 and the corresponding magnetic element 214 are pressed or actuated. In some embodiments, multiple sensors 240 adjacent to the magnetic element 214 during the course of rotation of the array component 230 may exceed the magnetomotive force threshold and move to a closed state when the button 212 is pressed or actuated. During operation, the one or more sensors 240 in a closed state when the button 212 is pressed or actuated may change as the instrument shaft 204 rotates.

In some embodiments, the arrangement 242 can be configured such that at least one sensor 240 does not experience sufficient magnetomotive force to exceed the magnetomotive force threshold of the sensor 240 to be in an open state when the button 212 and the corresponding magnetic element 214 are in a resting or unactuated position. In some applications, the arrangement 242 of the sensors 240 may prevent all the sensors 240 from being placed in a closed position when a respective button 212 is in an resting or unactuated position. During operation, the one or more sensors 240 in an open state when the button 212 is resting position may change as the instrument shaft 204 rotates. Therefore, in accordance with some embodiments, at least one sensor 240 may be changed to a closed state when a button 212 is pressed and at least one sensor 240 may be changed to an open state when a button 212 is in a resting position.

As illustrated, the sensors 240 may be placed in an arrangement 242 on a printed circuit board 232. In some embodiments, the sensors 240 are disposed in a circular arrangement 242. In some embodiments, the sensors 240 can be equidistantly spaced around the circumference of the printed circuit board 232. Optionally, a first set of sensors 240 can be disposed in an arrangement 242 on a first surface 231 of the printed circuit board 232. In some embodiments, a second set of sensors 240 can be disposed in an arrangement 242' on the second surface 233 of the printed circuit board 232. In some embodiments, the second arrangement 242' of sensors 240 are interposed between the first arrangement 242 of sensors 240. In some embodiments, the sensors 240 are disposed between an edge 236 and a cavity or opening 234 of the printed circuit board 232. The printed circuit board 232 may have a generally circular, annular, or ring shape. Optionally, the printed circuit board 232 can define channels 238 to allow shafts 226 to pass through and fasten the printed circuit boards 232 of the array component 230.

In some embodiments, the arrangement 242 can include six sensors 240 and the arrangement 242' can include five sensors 240. Optionally, the eleven sensors 240 can be evenly spaced (approximately every 32 degrees) to minimize angular spacing between the sensors 240, maximizing the number of sensors 240 capable of detecting the magnetomotive force of a respective magnetic element 214 when the button 212 is actuated. In some embodiments, the array component 230 may include additional sensors 240 to further minimize the angular spacing between the sensors 240. Optionally, the number of sensors 240 utilized by the array component 230 may vary.

In some embodiments, other aspects of the array component 230 and/or the corresponding magnetic element 214 can be configured such that at least one sensor 240 accurately detects and indicates the state of the respective button 212 as the array components 230 of the sensor array 220 rotate with the instrument shaft 204 and relative to the respective button 212. For example, the parameters of the sensor 240 may be altered or specified to adjust the magnetomotive force threshold of the sensor 240 such that at least one sensor 240 accurately detects and indicates the state of the respective button 212 during rotation of the array components 230. In another example, the size, strength, or other parameters of the magnetic elements 214 may be altered or specified to adjust the magnetomotive force applied to the sensor 240 such that at least one sensor 240 accurately detects and indicates the state of the respective button 212 during rotation of the array components 230. In some embodiments, the spacing and/or orientation of the magnetic elements 214 and/or the sensor 240 can be adjusted or modified to adjust the magnetomotive force applied to the sensor 240 such that at least one sensor 240 accurately detects and indicates the state of the respective button 212 during rotation of the array components 230.

Further, in some applications, the range of motion of the buttons 212 and/or the magnetic elements 214 can be adjusted to modify the magnetomotive force applied at one or more sensor 240 when the button 212 is in a resting position and the magnetomotive force applied at one or more switch when the button 212 is actuated, such that at least one sensor 240 accurately detects and indicates the state of the respective button 212 during rotation of the array components 230. In some embodiments, the range of motion of the magnetic elements 214 can be adjusted relative to the axis of rotation of the instrument shaft 204 to increase a difference between the applied magnetomotive force applied to a sensor 240 when the button 212 is in an unactuated state and the applied magnetomotive force applied to the sensor 240 when the button 212 is in an actuated state. In some embodiments, the range of motion of the buttons 212 may be reduced to provide a desired system response.

In some embodiments, the laparoscope 200 includes a controller to determine the state of the buttons 212a, 212b, 212c. In some embodiments, the controller analyzes the state of the sensors 240 of each of the array components 230a, 230b, 230c, to determine the state of each of the respective buttons 212a, 212b, 212c. In some applications, the controller utilizes a table lookup or algorithmic approach to compare the state of each of the sensors 240 to determine the state of a respective button 212. In some applications, the controller may monitor for a single sensor 240 of a array component 230 to move to a closed state to determine that a respective button 212 has been pressed. Optionally, the controller may monitor for multiple or a certain number of sensors 240 to move to a closed state to determine that a respective button 212 has been pressed. In some applications, the controller may monitor for changes in sensor 240 states to determine if a respective button 212 has been pressed or released. In some applications, the controller may filter sensors 240 that may be in a closed state when a button 212 is in a resting position. For example, the controller may determine a "baseline" status for each sensor 240 of a respective array component 230 (e.g. during an initialization process) to determine if any sensors 240 are in a closed state when a button 212 is in a resting position, and monitor sensors 240 identified in an initial open state that change to a closed state to determine when the button 212 is pressed.

Figure 27:
FIG. 27 illustrates a perspective view of a sensor array, in accordance with some embodiments.
Figure 28:
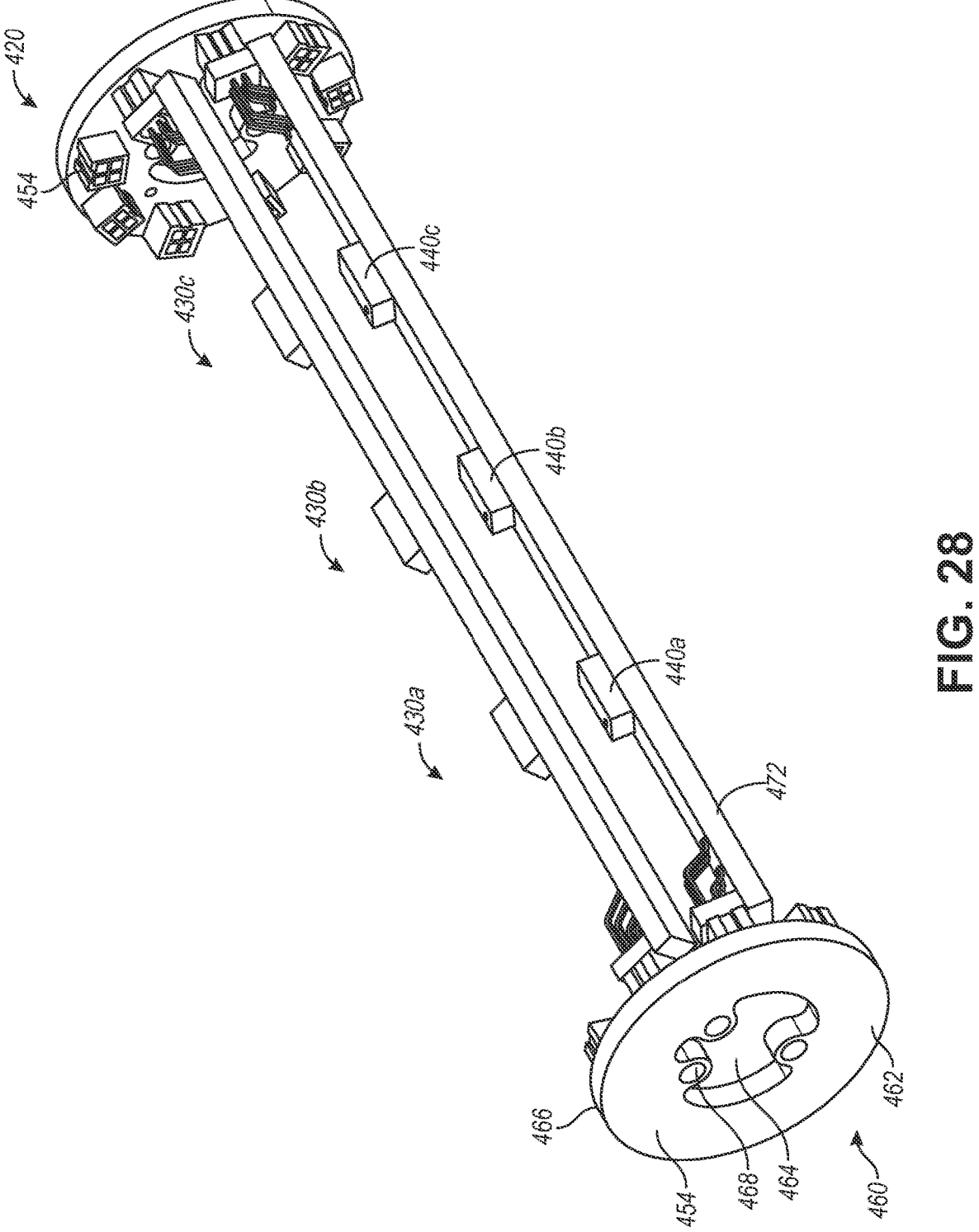
FIG. 28 illustrates a perspective view of a partial sensor array of FIG. 27.
Figures 29, 30:
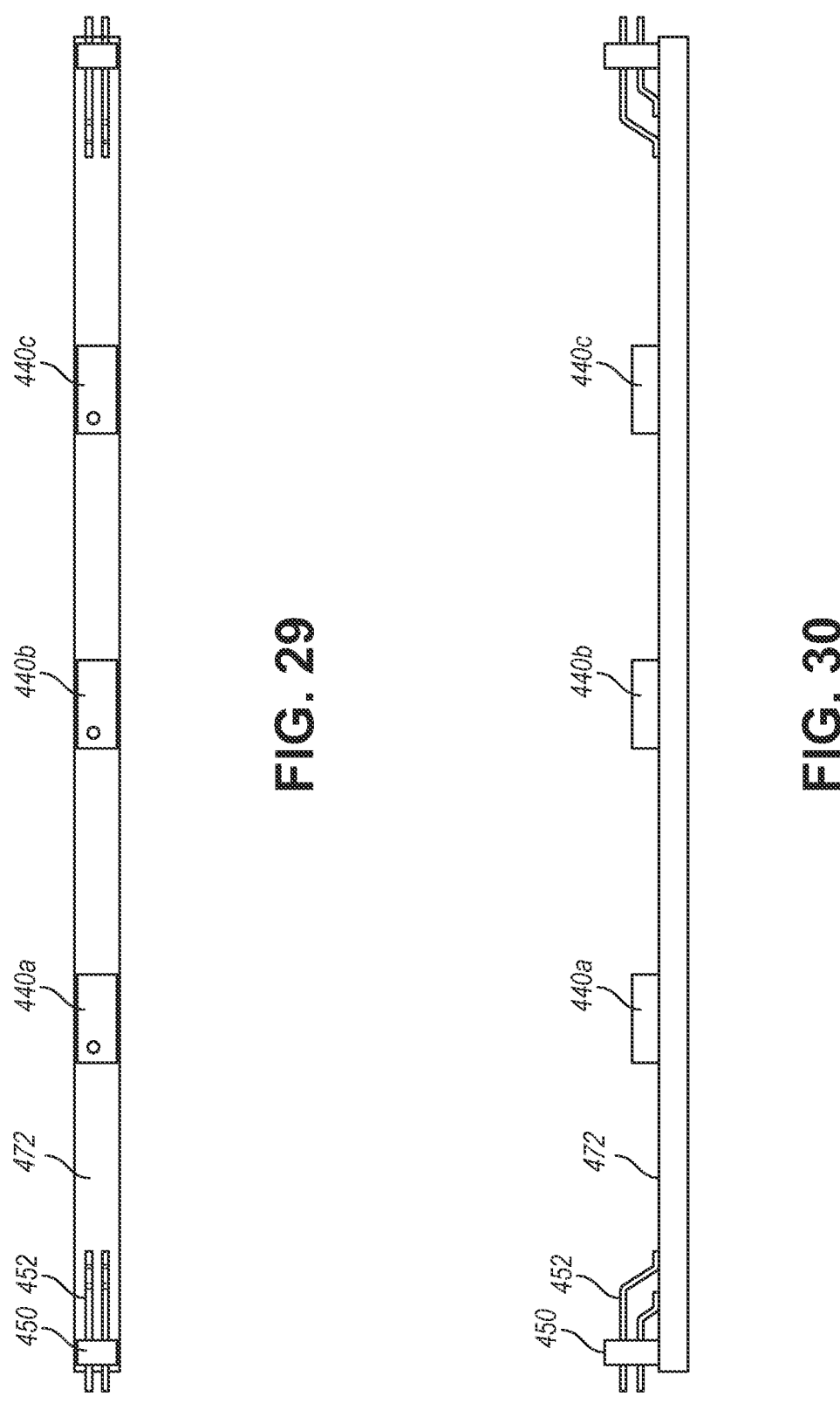
FIG. 29 illustrates a front elevation view of a printed circuit board of the sensor array of FIG. 27.
FIG. 30 illustrates a side elevation view of the printed circuit board of FIG. 27.

FIG. 27 illustrates a perspective view of a sensor array 420, in accordance with some embodiments. FIG. 28 illustrates a perspective view of a partial sensor array 420 of FIG. 27. FIG. 29 illustrates a front elevation view of a printed circuit board 472 of the sensor array 420 of FIG. 27. FIG. 30 illustrates a side elevation view of the printed circuit board 472 of FIG. 27. With reference to FIGS. 27-30, in some embodiments, a laparoscope can utilize a sensor array 420 to detect the position or state of one or more buttons. In some embodiments, certain features of the sensor array 420 may be similar to features of the sensor array 220 and may be referenced with similar reference numerals.

In the depicted example, the sensor array 420 can wirelessly detect the position, actuation, or state of the buttons of a laparoscope or other surgical instrument. In some embodiments, the sensor array 420 can detect changes in magnetic field to determine the state of the buttons. In the depicted example, the sensor array 420 includes one or more sensor sets 430a, 430b, 430c to detect the actuation or change of state of a respective button by detecting the change in magnetic field of the respective magnetic elements. As illustrated, each sensor set 430a, 430b, 430c can be aligned with a respective magnetic element to detect the state of the respective button. For example, each sensor set 430a, 430b, 430c can be aligned along the axis of rotation of the instrument shaft with a respective magnetic element to detect the state of the respective button. Optionally, the sensor array 420 can include more or fewer sets of sensors corresponding to the number of user interface elements or buttons.

Similar to sensor array 220, the sensor array 420 can be disposed within an instrument shaft, such as instrument shaft 204 described herein. In some embodiments, the sensor array 420 is sealed, isolated, or otherwise enclosed within the instrument shaft without compromising the integrity or otherwise breaching the instrument shaft. In the depicted example, the sensor array 420 can rotate with the instrument shaft, permitting the sensor array 420 to rotate relative to the buttons. As described herein, embodiments of the sensor array 420 can detect changes in magnetic field to determine the state of the buttons as the sensor array 420 rotates relative to the buttons.

In some embodiments, each sensor set 430a, 430b, 430c includes one or more sensors 440a, 440b 440c to detect a state of a respective button. In some embodiments, the sensors 440a, 440b 440c may include reed switches, hall effect sensors, and/or capacitive touch sensors.

In the depicted example, each sensor set 430a, 430b, 430c is configured to detect a change in magnetic field of a magnetic element (e.g. magnetic elements 214a, 214b 214c) to detect the position of a user input or button (e.g. buttons 212a, 212b, 212c). During operation, one or more sensors 440a, 440b 440c in each sensor set 430a, 430b, 430c can change in state (e.g. from an open state to a closed state) in response to a user input or button press to provide a corresponding signal to the laparoscope or the connected robotic system. As described with respect to sensor array 220, the sensors 440a, 440b 440c can be reed switches that are configured to move between a first state, such as an open state (i.e. open circuit) and a second state, such as a closed state (i. e. closed circuit), in response to an applied magnetic field or magnetomotive force.

In the depicted example, each sensor set 430a, 430b, 430c can include multiple sensors 440a, 440b, 440c to allow the each sensor set 430a, 430b, 430c to detect the state of a respective button as the sensor sets 430a, 430b, 430c rotate with the instrument shaft and relative to the respective buttons. In some embodiments, the sensors 440a, 440b, 440c of the sensor sets 430a, 430b, 430c and/or the corresponding magnetic elements can be configured such that at least one sensor 440a, 440b, 440c from each sensor set 430a, 430b, 430c accurately detects and indicates the state of the respective button as the sensor sets 430a, 430b, 430c of the sensor array 420 rotate with the instrument shaft and relative to the respective buttons.

Similar to the embodiment described with respect to sensor array 220, each sensor set 430a, 430b, 430c may include multiple sensors 440a, 440b, 440c in an arrangement, such that at least one sensor 440a, 440b, 440c from each sensor set 430a, 430b, 430c is adjacent to the respective magnetic element during the course of rotation experiences sufficient magnetic field or magnetomotive force to exceed the magnetomotive force threshold of the sensor 440a, 440b, 440c and move or change to a closed state when the button and the corresponding magnetic element are pressed or actuated.

As illustrated, the sensors 440a, 440b, 440c of each sensor set 430a, 430b, 430c may be placed in an arrangement around the central axis of rotation. In some embodiments, the sensors 440a, 440b, 440c of each sensor set 430a, 430b, 430c are disposed circumferentially around the central axis of rotation. As illustrated, each sensor set 430a, 430b, 430c is axially spaced apart along the central axis of rotation.

In the depicted example, the sensors 440a, 440b, 440c of each sensor set 430a, 430b, 430c are disposed on multiple printed circuit boards 472. In some embodiments, as illustrated, one sensor 440a, 440b, 440c, from each respective sensor set 430a, 430b, 430c is disposed on a single printed circuit board 472. In other words, sensors 440a, 440b, 440c, from different sensor sets are disposed on a common printed circuit board 472 and share a common angular alignment relative to the axis of rotation. In some embodiments, sensors 440a, 440b, 440c can be disposed on a radial surface of the printed circuit board 472. The printed circuit board 472 may have a generally elongated or slat shape. In the depicted example, printed circuit boards 472 are circumferentially disposed around the central axis of rotation.

As illustrated, the printed circuit boards 472 can be coupled to backplanes 460. In the depicted example, the printed circuit boards 472 can include connectors 450 to mechanically couple to mating connectors 454 of the backplanes 460. As illustrated, the connectors 450 can further facilitate electrical communication between the sensors 440a, 440b, 440c disposed on the printed circuit board 472 and the backplanes 460 via the connectors 454. The printed circuit board 472 can include traces or conductors 452 to facilitate an electrical connection between the sensors 440a, 440b, 440c via the printed circuit board 472 and the connector 450. In some embodiments, the backplanes 460 include or define a central cavity 464 and/or channels 468 to facilitate the passage of wiring and/or hardware.

In some embodiments, the each sensor set 430a, 430b, 430c can include nine sensors 440a, 440b, 440c disposed on nine printed circuit boards 472. In some embodiments, the sensors 440a, 440b, 440c of each sensor set 430a, 430b, 430c can be equidistantly spaced around the rotational axis (approximately every 40 degrees) to minimize angular spacing between the sensors 440a, 440b, 440c, and maximizing the number of sensors 440a, 440b, 440c capable of detecting the magnetomotive force of a respective magnetic element when the button is actuated. In some embodiments, the sensor sets 430a, 430b, 430c may include additional sensors 440a, 440b, 440c, to further minimize the angular spacing between the sensors 440a, 440b, 440c. Optionally, the number of sensors 440a, 440b, 440c utilized by each sensor set 430a, 430b, 430c may vary. Therefore, in some embodiments, the number of corresponding printed circuit boards 472 and backplane connectors 454 may vary accordingly.

As described herein, other aspects of the sensor sets 430a, 430b, 430c and/or the corresponding magnetic elements can be configured such that at least one sensor 440a, 440b, 440c accurately detects and indicates the state of the respective button as the sensor sets 430a, 430b, 430c of the sensor array 420 rotate with the instrument shaft and relative to the respective buttons.

3. Implementing Systems and Terminology

Implementations disclosed herein can advantageously provide systems, methods and apparatus for provide an added level of safety to a robot that interacts with humans, by allowing joints to be completely unlocked and repositioned even under complete electrical or software failure of the robot.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present inventions. Various modifications to these implementations will be readily apparent to those skilled in the art, and the generic principles defined herein may be applied to other implementations without departing from the scope of the inventions. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present inventions are not intended to be limited to the implementations shown herein but is to be accorded the widest scope consistent with the principles and novel features disclosed herein.

What is claimed is:

1. A sensor array to detect a position of a magnetic element, the sensor array comprising:
a printed circuit board, wherein the printed circuit board is configured to rotate about a rotation axis and relative to the magnetic element; and
a plurality of sensors disposed circumferentially about the rotation axis and coupled to the printed circuit board, the plurality of sensors being configured to rotate with the printed circuit board about the rotation axis and relative to the magnetic element, wherein at least one sensor of the plurality of sensors disposed at a selected circumferential position relative to the rotation axis is configured to change between an open state and a closed state in response to a change in the position of the magnetic element relative to the rotation axis.

2. The sensor array of claim 1, wherein each of the plurality of sensors are equidistantly spaced apart.

3. The sensor array of claim 1, wherein the printed circuit board defines a circular profile.

4. The sensor array of claim 1, further comprising a second plurality of sensors disposed circumferentially about the rotation axis and coupled to the printed circuit board.

5. The sensor array of claim 4, wherein the plurality of sensors is disposed on a first surface of the printed circuit board and the second plurality of sensors are disposed on an opposite second surface of the printed circuit board.

6. The sensor array of claim 5, wherein the sensors of the second plurality of sensors are interposed between the sensors of the plurality of sensors.

7. The sensor array of claim 1, wherein the printed circuit board comprises a plurality of elongated slats disposed circumferentially about the rotation axis and configured to rotate about the rotation axis and relative to the magnetic element, and each of the sensors are coupled to a respective elongated slat of the plurality of elongated slats.

8. The sensor array of claim 7, further comprising a second plurality of sensors coupled to a respective elongated slat of the plurality of elongated slats, wherein each of the sensors of the second plurality of sensors are laterally spaced apart along the rotation axis from the respective sensors of the plurality of sensors and at least one sensor of the second plurality of sensors disposed at a selected circumferential position relative to the rotation axis is configured to change between an open state and a closed state in response to a change in the position of a second magnetic element relative to the rotation axis.

9. A surgical instrument comprising:
an instrument shaft;
a tool drive adapter comprising:
a housing disposed around a portion of the instrument shaft, wherein the instrument shaft is rotatably coupled to the tool drive adapter such that the instrument shaft is rotatable about a rotation axis relative to the housing; and
an actuator coupled to the housing, wherein actuation of an actuator controls a function of the surgical instrument; and
a sensor array disposed within the instrument shaft, the sensor array comprising:
a printed circuit board fixedly coupled to an interior of the instrument shaft such that the printed circuit board is configured to rotate with the instrument shaft about the rotation axis and relative to the actuator of the tool drive adapter; and
a plurality of sensors disposed circumferentially about the rotation axis and fixedly coupled to the printed circuit board such that the plurality of sensors is configured to rotate with the printed circuit board about the rotation axis and relative to the actuator of the tool drive adapter, wherein at least one sensor of the plurality of sensors disposed at a selected circumferential position relative to the rotation axis is configured to provide a signal corresponding to actuation of the actuator.

10. The surgical instrument of claim 9, wherein the plurality of sensors comprises a plurality of reed switches.

11. The surgical instrument of claim 9, further comprising a second plurality of sensors disposed circumferentially about the rotation axis.

12. The surgical instrument of claim 9, wherein the plurality of sensors are disposed on a first surface of the printed circuit board and a second plurality of sensors are disposed on an opposite second surface of the printed circuit board.

13. The surgical instrument of claim 12, wherein the sensors of the second plurality of sensors are interposed between the sensors of the plurality of sensors.

14. The surgical instrument of claim 9, wherein the tool drive adapter comprises a second actuator coupled to the housing and actuation of the second actuator controls a second function of the surgical instrument, and at least one sensor of a second plurality of sensors disposed at a selected circumferential position relative to the rotation axis is configured to provide a signal corresponding to actuation of the second actuator.

15. The surgical instrument of claim 9, wherein the instrument shaft comprises a laparoscopic instrument.

16. The surgical instrument of claim 9, wherein the housing is configured to attach to a robotic surgical system.

17. A surgical instrument comprising:
an instrument shaft;
a tool drive adapter comprising:
a housing disposed around a portion of the instrument shaft, wherein the instrument shaft is rotatable about a rotation axis relative to the housing; and
an actuator coupled to the housing, wherein actuation of an actuator controls a function of the surgical instrument; and a sensor array disposed within the instrument shaft, the sensor array comprising:

a plurality of elongated printed circuit boards disposed circumferentially about the rotation axis and fixedly coupled to an interior of the instrument shaft such that the plurality of elongated printed circuit boards is configured to rotate with the instrument shaft about the rotation axis and relative to the actuator of the tool drive adapter; and a plurality of sensors, wherein each sensor of the plurality of sensors is fixedly coupled to a respective elongated printed circuit board of the plurality of elongated printed circuit boards such that the sensor is configured to rotate with the respective elongated printed circuit board about the rotation axis and relative to the actuator of the tool drive adapter, wherein at least one sensor of the plurality of sensors disposed at a selected circumferential position relative to the rotation axis is configured to provide a signal corresponding to actuation of the actuator.

18. The surgical instrument of claim 17, wherein the sensor array further comprises a backplane coupled to the plurality of elongated printed circuit boards.

19. The surgical instrument of claim 17, wherein the tool drive adapter comprises a second actuator coupled to the housing and actuation of the second actuator controls a second function of the surgical instrument, and the sensor array further comprising a second plurality of sensors coupled to a respective elongated printed circuit board of the plurality of printed elongated circuit boards, wherein each of the sensors of the second plurality of sensors are laterally spaced apart along the rotation axis from the respective sensor of the plurality of sensors and at least one sensor of the second plurality of sensors disposed at a selected circumferential position relative to the rotation axis is configured to provide a signal corresponding to actuation of the second actuator.

20. The surgical instrument of claim 17, wherein the plurality of sensors comprises a plurality of reed switches.

* * * * *